United States Patent
Schneider et al.

(10) Patent No.: US 6,427,079 B1
(45) Date of Patent: Jul. 30, 2002

(54) POSITION AND ORIENTATION MEASURING WITH MAGNETIC FIELDS

(75) Inventors: Mark R. Schneider, Williston; Christopher D. Conover, Underhill, both of VT (US)

(73) Assignee: CorMedica Corporation, Natick, MA (US)

( * ) Notice: Subject to any disclaimer, the term of this patent is extended or adjusted under 35 U.S.C. 154(b) by 0 days.

(21) Appl. No.: 09/370,208

(22) Filed: Aug. 9, 1999

(51) Int. Cl.[7] ............................................... A61B 5/05
(52) U.S. Cl. ....................... 600/424; 600/427; 600/429; 606/130; 324/244; 324/260
(58) Field of Search ............................... 600/424, 407, 600/409, 410, 417, 411, 415, 425, 429, 481, 508; 606/130; 324/244, 219, 246, 248, 260

(56) References Cited

U.S. PATENT DOCUMENTS

| | | |
|---|---|---|
| 3,868,565 A | 2/1975 | Kuipers |
| 3,967,201 A | 6/1976 | Rorden |
| 4,054,881 A | 10/1977 | Raab |
| 4,287,809 A | 9/1981 | Egli et al. |
| 4,314,251 A | 2/1982 | Raab |
| 4,328,548 A | 5/1982 | Crow et al. |
| 4,346,384 A | 8/1982 | Raab |
| 4,394,831 A | 7/1983 | Egli et al. |
| 4,396,885 A | 8/1983 | Constant |
| 4,613,866 A | 9/1986 | Blood |
| 4,622,644 A | 11/1986 | Hansen |
| 4,642,786 A | 2/1987 | Hansen |
| 4,710,708 A | 12/1987 | Rorden et al. |
| 4,737,794 A | 4/1988 | Jones |
| 4,742,356 A | 5/1988 | Kuipers |
| 4,829,250 A | 5/1989 | Rotier |
| 4,849,692 A | 7/1989 | Blood |
| 4,945,305 A | 7/1990 | Blood |
| 4,945,395 A | 7/1990 | Suehiro |
| 5,042,486 A | 8/1991 | Pfeiler et al. |
| 5,099,845 A | 3/1992 | Besz et al. |
| 5,151,856 A | * 9/1992 | Halmann et al. ...... 364/413.03 |

(List continued on next page.)

FOREIGN PATENT DOCUMENTS

| | | |
|---|---|---|
| EP | 655138 B1 | 4/1998 |
| WO | WO94/04938 A1 | 3/1994 |
| WO | WO96/05768 A1 | 2/1996 |
| WO | WO97/32179 A1 | 9/1997 |
| WO | WO98/36236 A1 | 8/1998 |
| WO | WO 00/68637 | 4/2000 |

OTHER PUBLICATIONS www.tno.nl/instit/bouw/project/gem/results/wp2/HTML2300/nodes 89–123, Sep. 10, 1998.

"Algorithms For Magnetic Helmet–Mounted Sight," by Frederick H. Raab, C. Chip Brewster, Frederick L. Stone and William F. Mackin, Green Mountain Radio Research Company, Colchester, Vermont, AL/CF–TR–1993–0077, May 1993.

Primary Examiner—Marvin M. Lateef
Assistant Examiner—Jeoyuh Lin
(74) Attorney, Agent, or Firm—Downs Rachlin Martin PLLC; William L. Feeney, Esq.

(57) ABSTRACT

Splines of magnetic field values are used by a processor to determine location parameters in a remote location determination system. The location determination system is used on a laser catheter that is operable to perform myocardial revascularization. An automatic calibration technique compensates for any variations in gain in a sensor and related components. Methods for reducing the effects of eddy currents in surrounding conductive objects are used in electromagnetic position and orientation measurement systems.

35 Claims, 17 Drawing Sheets

U.S. PATENT DOCUMENTS

| | | |
|---|---|---|
| 5,172,056 A | 12/1992 | Voisin |
| 5,211,165 A | 5/1993 | Dumoulin et al. |
| 5,273,025 A | 12/1993 | Sakiyama et al. |
| 5,307,072 A | 4/1994 | Jones, Jr. |
| 5,347,289 A | 9/1994 | Elhardt |
| 5,377,678 A | 1/1995 | Dumoulin et al. |
| 5,425,367 A | 6/1995 | Shapiro et al. |
| 5,429,132 A | 7/1995 | Guy et al. |
| 5,443,066 A | 8/1995 | Dumoulin et al. |
| 5,453,686 A | 9/1995 | Anderson |
| 5,480,422 A | 1/1996 | Ben-Haim |
| 5,558,091 A | 9/1996 | Acker et al. |
| 5,565,909 A | 10/1996 | Thibadeau et al. |
| 5,586,982 A | 12/1996 | Abela |
| 5,592,939 A | 1/1997 | Martinelli |
| 5,600,330 A | 2/1997 | Blood |
| 5,622,169 A | 4/1997 | Golden et al. |
| 5,640,170 A | 6/1997 | Anderson |
| 5,729,129 A * | 3/1998 | Acker .................. 324/207.12 |
| 5,730,741 A | 3/1998 | Horzewski et al. |
| 5,752,513 A | 5/1998 | Acker et al. |
| 5,762,064 A | 6/1998 | Polvani |
| 5,769,843 A | 6/1998 | Abela et al. |
| 5,782,765 A | 7/1998 | Jonkman |
| 5,807,388 A | 9/1998 | Jeevanandam et al. |
| 5,824,005 A | 10/1998 | Motamedi et al. |
| 5,830,210 A | 11/1998 | Rudko et al. |
| 6,059,718 A * | 5/2000 | Taniguchi et al. .......... 600/117 |

* cited by examiner

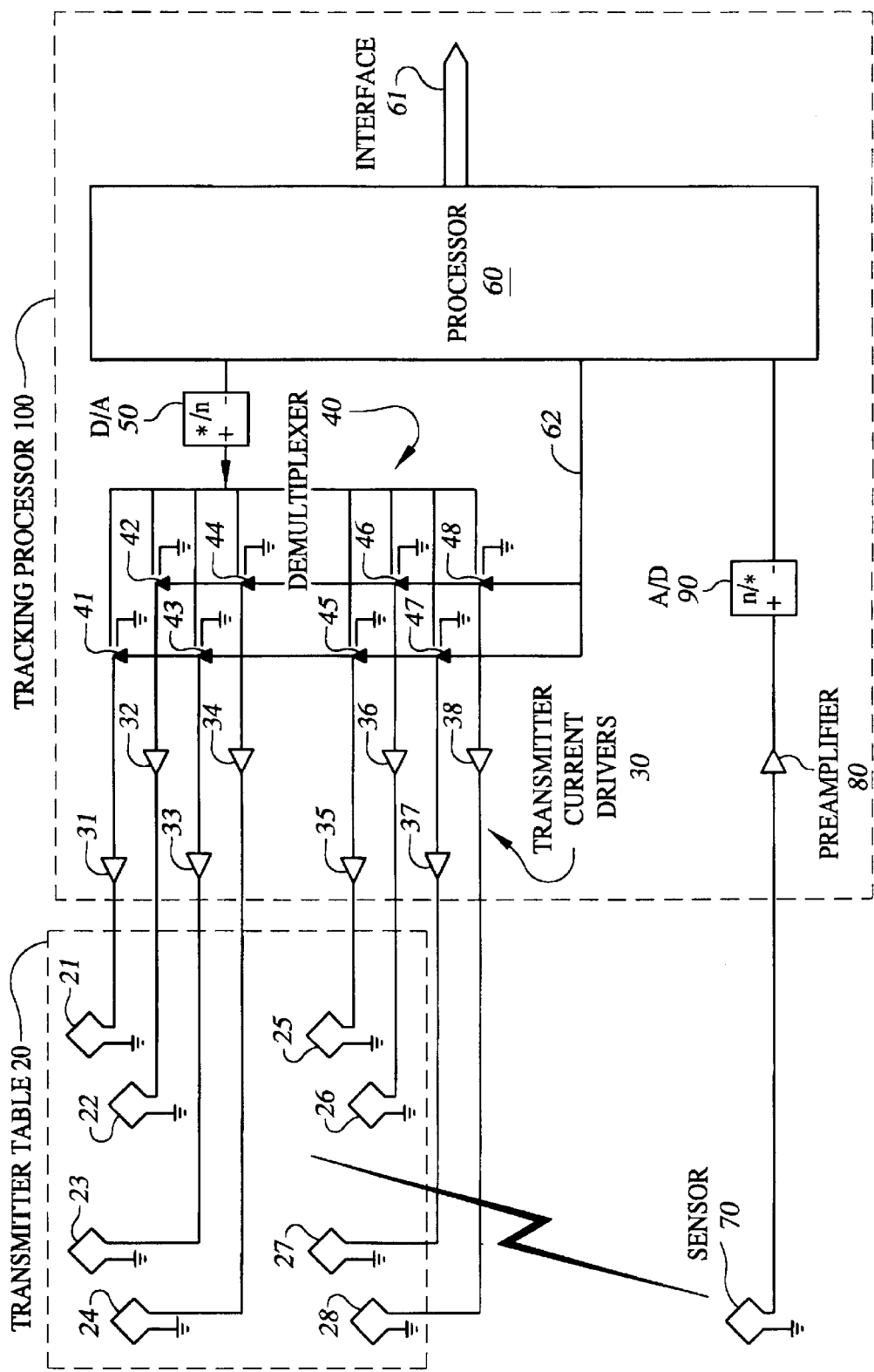

FIG.7b1
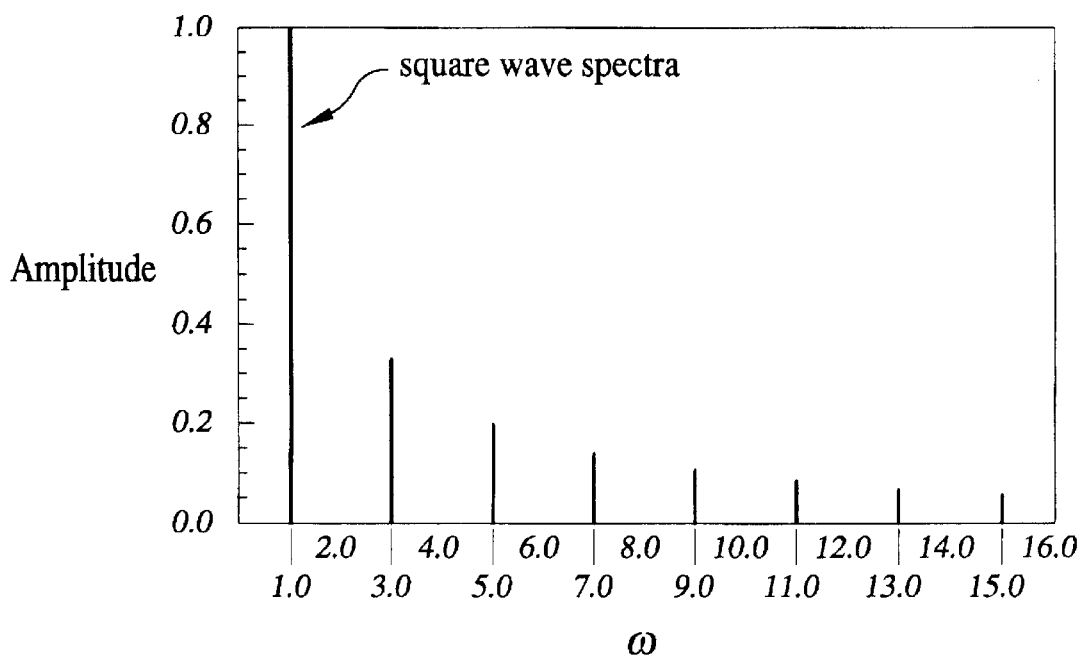
FIG.7b2
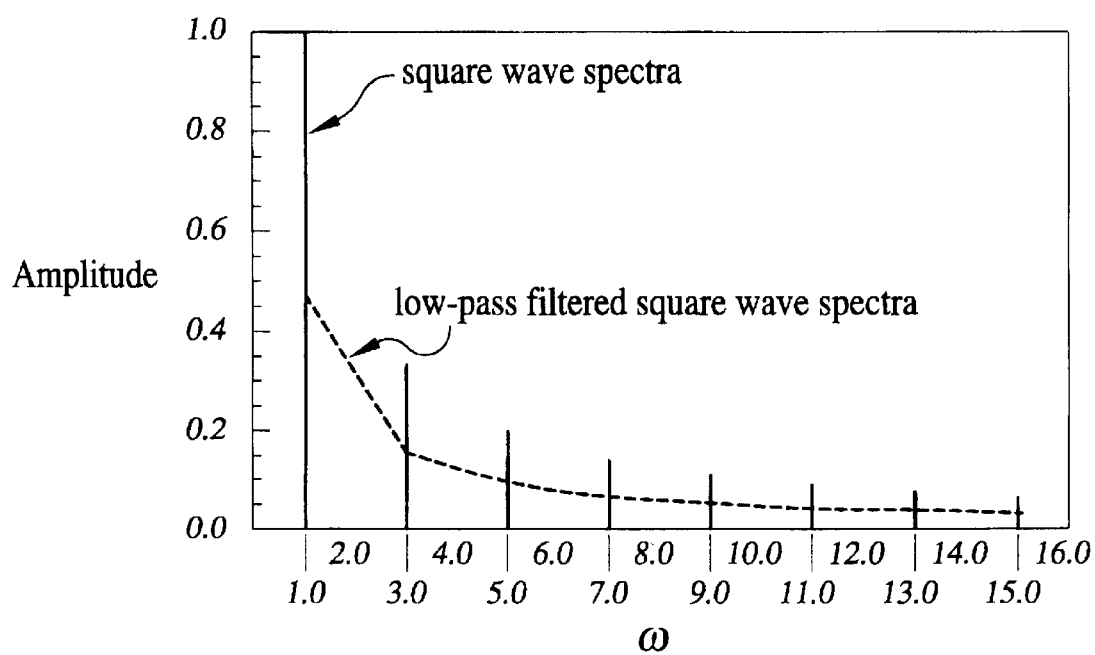

FIG.7b3
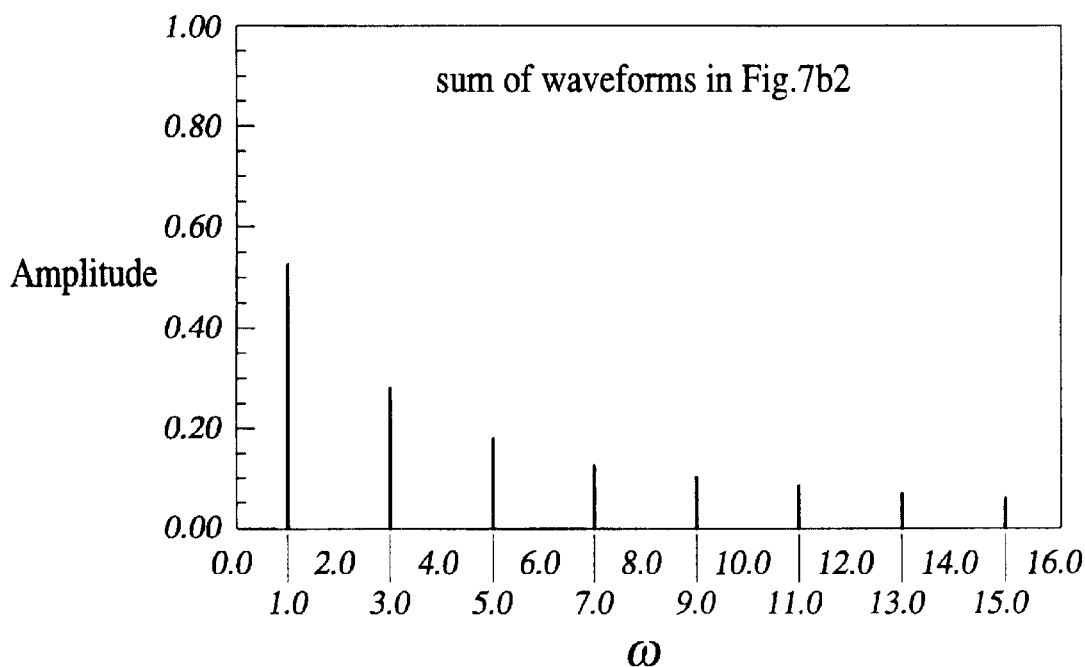
FIG.8a
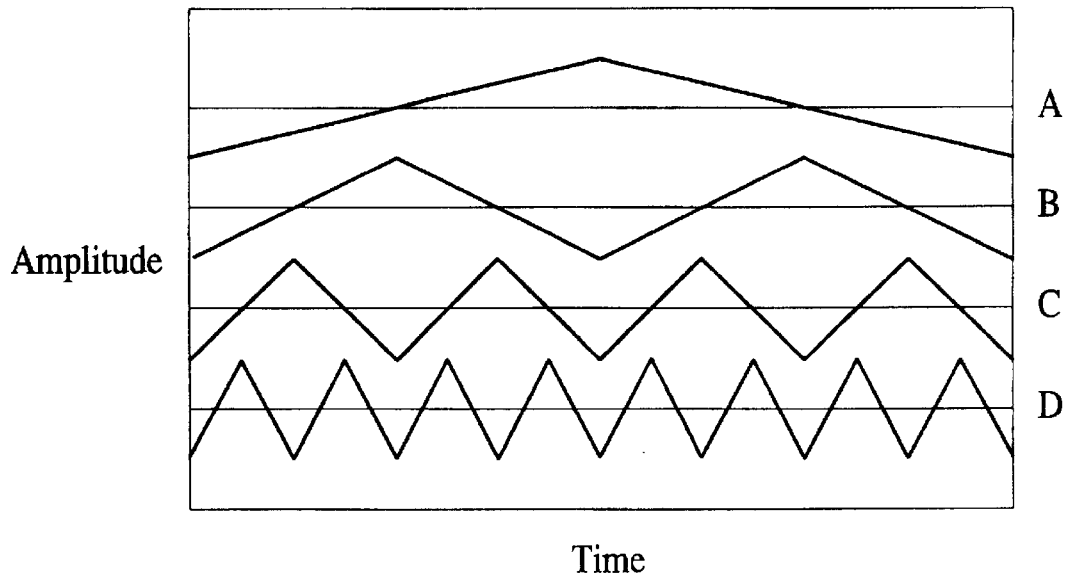

POSITION AND ORIENTATION MEASURING WITH MAGNETIC FIELDS

BACKGROUND OF THE INVENTION

The present invention relates to a system and method for determining the position and orientation of a remote object relative to a reference coordinate frame using magnetic fields. More specifically, the position and orientation of a medical device, such as a catheter, within a patient is determined with a relatively high level of accuracy.

Determining the position and orientation of objects in free space has many applications. The applications having determination of location parameters include catheter tracking, digitizing objects, and virtual reality among others. (As used herein, location parameters include position and orientation information.) One method that has become successful in these applications relies on the electromagnetic coupling between a source of magnetic fields and the sensing of such fields. Variations include AC and pulsed-DC magnetic field generation and single and multiple axes sensing and generating elements. Examples of AC systems with a plurality of generating and sensing elements are disclosed in Kuipers (U.S. Pat. No. 3,868,565), Raab (U.S. Pat. No. 4,054,881) and Jones (U.S. Pat. No. 4,737,794) among others.

Prior systems are generally hindered by inaccuracies in the presence of conductive materials within the tracking environment. These inaccuracies are caused by eddy current flow in the conductive materials. Eddy currents are due to the time variation of the AC magnetic field, which induces an electric field. This electric field, in turn, causes an electric current (eddy current) to flow in the conducting medium. These eddy currents, in turn, generate their own magnetic field. The eddy currents introduce inaccuracies which prior techniques generally ignore.

Methods to improve the accuracy of these systems include characterizing the environment and applying previously stored corrections. The corrections are applied based on the system's present position and orientation (U.S. Pat. No. 4,622,644 Hansen and U.S. Pat. No. 4,945,305 Blood, among others). Other methods include signal generation and processing schemes that allow the induced eddy currents, the source of the inaccuracy, to be eliminated. Such systems utilize pulsed-DC or multi-frequency excitations.

Examples of pulsed-DC systems with a plurality of generating and sensing elements are disclosed in Blood (U.S. Pat. No. 4,945,305) and Anderson (U.S. Pat. No. 5,453,686). The use of pulsed-DC systems reduces the effects of eddy currents thereby improving accuracy in the presence of conductive materials within the tracking systems environment. The disadvantage to pulsed-DC systems is that they operate only in a time division multiplexed mode. Other drawbacks sometimes include the need for bulky and more complex active sensing devices (i.e., as compared to sensors used in AC systems). The Blood sensing devices measure fields from DC on up and are thus sensitive to the earth's magnetic field, which must be compensated for. It also means that such systems cannot work near medical instruments that operate with large DC magnetic fields, such as magnetic manipulators. The Blood system removes eddy current induced inaccuracies by applying a DC excitation signal to a field generator and then curve fitting the decay to extrapolate the final sensed value. The Anderson system eliminates the use of DC sensitive field sensing elements and consequently reduces the complexity of the hardware. His signal processing scheme removes eddy current induced inaccuracies by applying a DC excitation signal to a field generator and integrating the sensed waveform from an AC sensor. This method integrates out the eddy current inaccuracies.

Some prior DC approaches require an active magnetic sensor that is complex, bulky, and has a poor signal to noise ratio compared to passive AC magnetic sensors. They are further complicated by the fact that the sensor is sensitive to the earth's magnetic field and processing steps must be included to eliminate the earth's magnetic field. This comes at the expense of system measurement update rate. Some approaches overcome or reduce some of the disadvantages, but must wait for the eddy currents to die out before determining the value of the field without the eddy currents deleterious effects. This too comes at the expense of system measurement update rate.

Another method for improving accuracy in the presence of conductive materials is disclosed in Rotier, U.S. Pat. No. 4,829,250. This AC method with a plurality of generating and sensing elements utilizes multi-frequency excitation of the field generator. Eddy current inaccuracies are a function of frequency. This knowledge is utilized by extrapolating to DC a curve fit from a higher frequency to a lower frequency to determine the yaw and pitch angles about a line-of-sight axis, which does not include position.

A method further removed from the previously noted techniques for improving accuracy in the presence of conductive materials is disclosed in Elhardt, U.S. Pat. No. 5,347,289. A rotating magnetic field vector of known frequency is generated from a plurality of field generators. Multiple sensors, each with a plurality of sensing elements are mounted on the object to be tracked. A measurement of the time required for the field vector to pass through a reference point and then through a sensor allows the position of the sensor to be determined. Using multiple sensors mounted in known proximity to one another allows the determination of the orientation of the sensors.

Tracking or determination of position and orientation techniques often uses a model of the magnetic fields generated by a specific geometry coil. For example, the present inventor's in U.S. patent application Ser. No. 08/996,125, filed on Dec. 12, 1997, entitled "MEASURING POSITION AND ORIENTATION USING MAGNETIC FIELDS," now U.S. Pat. No. 6,073,043, assigned to the assignee of the present application, and hereby incorporated by reference in its entirety, use a model of magnetic fields based on their geometry and using a least squares minimization technique. The model took into account the coil dimensions, coil placement and coil orientation. In practice, these coil parameters were determined by measuring the magnetic field at known positions and orientations. Using this data allowed the coil parameters to be determined. These parameters were then utilized in the method to determine position and orientation.

Most magnetic tracking that provide five or six-degree of freedom measurements (the difference usually being whether senor roll is determined) utilize a model of one form or another for the magnetic field generators. Dipole and enhanced dipole models are found in Jones (U.S. Pat. Nos. 4,737,794 and 5,307,072), Blood (U.S. Pat. No. 4,945,305), Dumoulin (U.S. Pat. Nos. 5,211,165 and 5,377,678), Bladen (WO 94/04938) and Ben-Haim (WO96/05768), among others. Other models are found in Blood (U.S. Pat. No. 5,600, 330) and Acker (U.S. Pat. No. 5,752,513) which use a line segment current source whose field varies inversely with range. These models fall apart near the vertices of the field generators. Still other models are found in Acker (U.S. Pat.

No. 5,558,091) and Martinelli (U.S. Pat. No. 5,592,939) which use quasi-linear/uniform field generation, among others. Martinelli also uses a look up table as part of his method to determine position and orientation. The look up table is filled with magnetic field data that is generated by theoretical means (based on a model). Depending on the degree of accuracy required in a specific position and orientation-measuring situation, the modeling technique may be satisfactory. However, such modeling techniques generally are subject to errors in the hardware, including distortion, non-linearity, cross coupling, and environmental factors such as fixed metal distortions.

Another source of possible errors or complications in a position and orientation systems in sensitivity to the gain of the sensors. Depending on the type of sensors and related components used, the gain of a particular unit may vary with ambient conditions, e.g., temperature, with aging of components, and other changed circumstances. Manufacturing tolerances can also cause one sensor and associated components to have a different gain than another sensor and associated components.

One way to take into account the variation in gain due to manufacturing tolerances is to measure the gain upon manufacture and store that value. However, that does not correct for changed circumstances. Another technique could be to take a test measurement to calibrate the unit for the gain of the sensor and related components. However, that complicates the measurement process.

OBJECTS AND SUMMARY OF THE INVENTION

Accordingly, it is a primary object of the present invention to provide a new and improved method and system with position and orientation determination with improved accuracy.

A more specific object of the present invention is to provide position and orientation determination for a catheter or other medical device inserted into a patient.

A further object of the present invention is to provide position and orientation determination which avoids or minimizes inaccuracies from eddy currents.

Yet another object of the present invention is to provide position and orientation determination with a minimum amount of errors from hardware problems or anomalies.

A further object of the present invention is to provide position and orientation determination with automatic calibration of the system for the gain of the sensors and related components.

The above and other features of the present invention which will be more readily understood when the following detailed description is considered in conjunction with the accompanying drawings are realized by a remote object location determining system with a generation subsystem having at least one transducer operable to produce an electromagnetic field and a sensing subsystem having at least one transducer operable to sense an electromagnetic field produced by the generation subsystem. A driver is operable to apply excitation waveforms to the generation subsystem. A processor is operably connected to receive sensor signals from the sensing subsystem and determine at least two location parameters by comparing measured magnetic field values to a function of splines corresponding to magnetic field values. At least one of the generation subsystem and the sensing subsystem has a plurality of transducers.

The processor has stored splines from measurements taken using known locations prior to using the system for determining unknown location parameters. The processor uses an iteration technique to determine the at least two location parameters. The generation subsystem includes a plurality of transducers operable to produce electromagnetic fields and the driver sequentially drives different transducers of the generation subsystem in a multiplexing operation.

The system is a medical system for use on a patient with one of the generating subsystem and sensing subsystem inside the patient and the other of the generating subsystem and sensing subsystem outside the patient.

The system further comprises a catheter operable for endomyocardial revascularization and wherein one of the generation subsystem and sensing subsystem is on or in the catheter.

The processor has a plurality of magnetic field values stored from initial measurements and determines location parameters by comparing measured magnetic field values to a function of stored splines.

In another aspect of the invention, the processor determines gain in the sensing subsystem automatically and determines location parameters independent from any variations in the gain of the sensing subsystem.

In another aspect of the invention, the processor minimizes inaccuracies in the location parameters by performing eddy current compensation, thus reducing or eliminating inaccuracies that would otherwise be introduced by eddy currents in the vicinity of the sensing subsystem and the generation subsystem.

The system is a medical system for use on a patient, the location parameters providing information used in a process of treating a patient.

The catheter is more specifically operable for endomyocardial revascularization. The catheter is a laser catheter operable for endomyocardial revascularization.

The present invention may alternately be described as a remote object location determining system with:
  a generation subsystem having at least one transducer operable to produce an electromagnetic field;
  a sensing subsystem having at least one transducer operable to measure an electromagnetic field produced by the generation subsystem;
  a driver operable to apply excitation waveforms to the generation subsystem; and
  a processor operably connected to receive sensor signals from the sensing subsystem, the processor operable to determine at least two location parameters of a relationship between the generation subsystem and the sensing subsystem. The processor determines gain in the sensing subsystem automatically and determines location parameters independent from any variations in the gain of the sensing subsystem. At least one of the generation subsystem and the sensing subsystem has a plurality of transducers.

In another aspect of the invention, the system is a medical system for use on a patient, the location parameters providing information used in a process of treating a patient. The medical system is operable for use on a patient with one of the generating subsystem and sensing subsystem inside the patient and the other of the generating subsystem and sensing subsystem outside the patient. A catheter is part of the system and one of the generation subsystem and sensing subsystem is on or in the catheter. The catheter is operable for endomyocardial revascularization. The catheter is a laser catheter.

In another aspect of the invention, the excitation waveforms are selected from the group consisting of a ramp waveform and a triangular waveform. At least one of the generation subsystem and the sensing subsystem has a plurality of transducers and wherein the processor minimizes inaccuracies in the location parameters by performing eddy current compensation, thus reducing or eliminating inaccuracies that would otherwise be introduced by eddy currents in the vicinity of the sensing subsystem and the generation subsystem.

In another aspect of the invention, the processor is operably connected to receive sensor signals from the sensing subsystem, and to determine at least two location parameters by comparing measured magnetic field values to a function of splines corresponding to magnetic field values.

The present invention may alternately be described as a remote object location determining system with:

a generation subsystem having at least one transducer operable to produce an electromagnetic field;

a sensing subsystem having at least one transducer operable to sense an electromagnetic field produced by the generation subsystem;

a driver operable to apply excitation waveforms to the generation subsystem, the excitation waveforms being selected from the group consisting of a ramp waveform and a triangular waveform; and a processor operably connected to receive sensor signals from the sensing subsystem, the processor operable to determine at least two location parameters of a relationship between the generation subsystem and the sensing subsystem; and wherein at least one of the generation subsystem and the sensing subsystem has a plurality of transducers and wherein the processor minimizes inaccuracies in the location parameters by performing eddy current compensation, thus reducing or eliminating inaccuracies that would otherwise be introduced by eddy currents in the vicinity of the sensing subsystem and the generation subsystem.

The generation subsystem includes a plurality of transducers operable to produce electromagnetic fields and wherein the driver sequentially drives different transducers of the generation subsystem in a multiplexing operation.

The processor performs eddy current compensation by a non-extrapolated calculating of a response at infinite time of the sensor signals.

The system is a medical system for use on a patient with one of the generating subsystem and sensing subsystem inside the patient and the other of the generating subsystem and sensing subsystem outside the patient. The system has a catheter operable for endomyocardial revascularization and one of the generation subsystem and sensing subsystem is on or in the catheter.

The processor is operably connected to receive sensor signals from the sensing subsystem, and to determine at least two location parameters by comparing measured magnetic field values to a function of splines corresponding to magnetic field values.

The processor determines gain in the sensing subsystem automatically and determines location parameters independent from any variations in the gain of the sensing subsystem.

BRIEF DESCRIPTION OF THE DRAWINGS

The above and other features of the present invention will be more readily understood when the following detailed description is considered in conjunction with the accompanying drawings wherein like characters represent like parts throughout the several views and in which:

FIG. 2 is a simplified schematic of some of components of a position and orientation determination system according to the present invention;

FIG. 3A is a time graph of the pattern of excitation of generator transducers, whereas

FIG. 7A is an illustration of three waveforms occurring in operation of the present invention, whereas FIGS. 7B1, 7B2, and 7B3 show frequency distributions of the three different waveforms of FIG. 7A;

FIG. 8A shows four waveforms used with the present invention, whereas

DETAILED DESCRIPTION

Eddy Current Errors

Figure 1A:
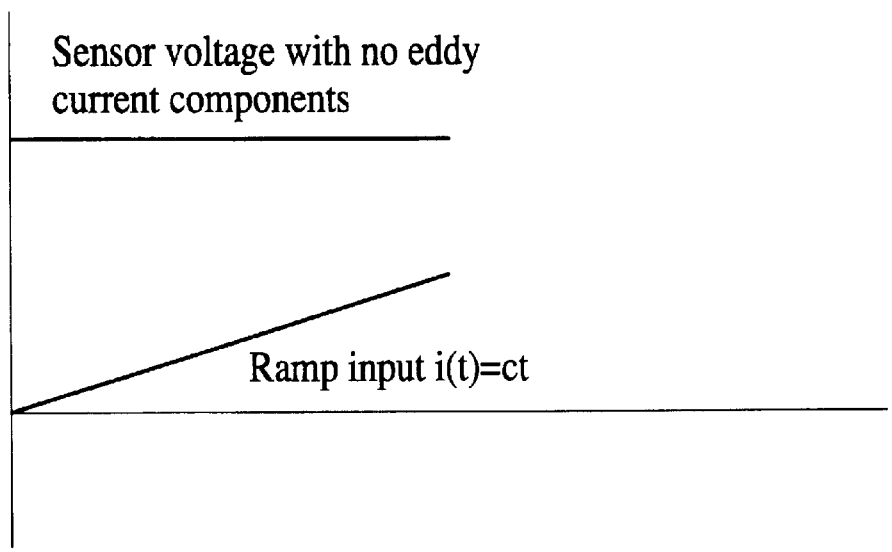
FIGS. 1A and 1B are time graphs of an input and a sensor signal used to illustrate effect of eddy currents.

Before discussing details of the invention, some explanation of eddy current errors will initially be given. The induced sensor voltage due to a changing magnetic field is given by:

$$v(t) = -\frac{\partial}{\partial t}\int_S \overline{B} \cdot d\overline{S} \tag{1}$$

where v(t) is the induced voltage and $\overline{B}$ is the magnetic flux density in the direction of $\overline{S}$, the surface that encloses $\overline{B}$ (in all cases, the sensor surface area). $\overline{B}$ is proportional to the current flowing in the field generator element. Electromagnetic tracking systems with multiple B-field generating elements can time multiplex the B-field generators to distinguish the induced sensor signals generated by each generator. This is the only method that can presently be used with pulsed-DC electromagnetic tracking systems. The use of a ramp waveform will now be used to illustrate a new method of removing eddy current distortion without using a pulsed-DC excitation as in Blood or Anderson patents. The Laplace transform of a ramp of current i(t)=ct can be written as:

$$I(s) = \frac{c}{s^2} \quad (2)$$

where c is the slope of the ramp (or the current value at time t). C is determined in the system by a calibration of the current source. The Laplace transform of a time varying signal is related to its Fourier transform, and is a function of the frequency components comprising the signal. It is useful in transient analysis, as will be seen shortly.

It is known that eddy currents induced in conductive media can be modeled by low-pass filter functions. The response of a sensor due to the field generator B-field and the B-fields due to eddy currents can be written succinctly in terms of the Laplace transform as:

$$V_{sensor}(s) = -sI(s)\left[k + \sum_{j=1}^{p} \frac{a_j}{s+b_j}\right] \quad (3)$$

where $V_{senor}$ (s) is the Laplace transform of the induced voltage at the sensor; I(s) is the Laplace transform of the current producing the magnetic field; k is proportional to the magnitude of the induced voltage due to I(s) and is a function of range between the sensing element and the field generator; $a_j$ is proportional to the magnitude of the induced voltage due to eddy current j and is a function of range between the sensing element and the conductive material; and $b_j$ is the −3 dB corner frequency that is a characteristic of the $j^{th}$ conducting medium which is supporting the eddy current. The "sI(s)" term can be interpreted as the derivative of the current which is being sensed, and is thus equivalent to (1).

It has been found that for most practical purposes modeling the environment with two eddy currents (p=2) provides sufficient accuracy for almost all electromagnetic tracking applications. Of course p may be greater than or less than 2 depending on the situation, and an adaptive method for setting p will be disclosed.

Plugging (2) into (3) with p=2 (for example) and taking the inverse Laplace transform yields:

$$v_{sensor}(t) = ck + \frac{ca_1}{b_1}[1 - e^{-b_1 t}] + \frac{ca_2}{b_2}[1 - e^{-b_2 t}] \quad (4)$$

Figure 1B:
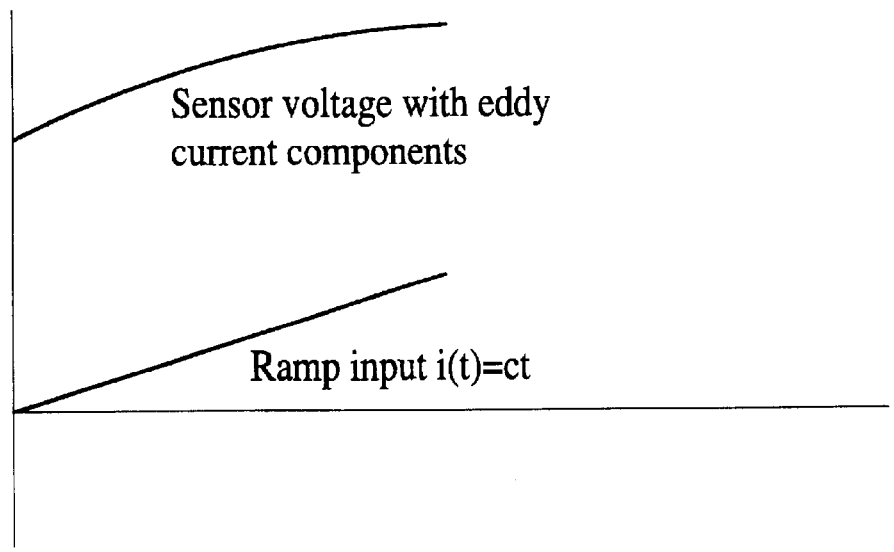

A typical response without and with eddy currents is shown in FIGS. 1a and 1b, respectively. Collecting a minimum of 2p+1 points along the induced voltage curve allows us to fit the data points to (4) using a least squares approach.

The least squares problem approach is: given m functions $f_1, f_2, \ldots, f_m$ of the n variables $x_1, x_2, \ldots, x_n$, with m≧n, find values for $x_1, x_2, \ldots, x_n$ that solve the nonlinear least squares problem $$\min\left\{\sum_{i=1}^{m} f_i(x)^2 : x \in R^n\right\} \quad (5)$$

Many methods exist for tackling these problems. The predominant methods require the evaluation of the Jacobian (a matrix of partial derivatives of the equations with respect to the unknowns), either explicitly or by finite differences and sometimes requiring the evaluation of the Hessian (a matrix of second partial derivatives of the equations with respect to the unknowns). These methods are often referred to as Newton methods, gradient methods or steepest descent methods or variations on that theme. U.S. Pat. No. 4,737,794 Jones, U.S. Pat. No. 5,592,939 Martinelli, U.S. Pat. No. 5,600,330 Blood, and U.S. Pat. No. 5,377,678 Dumoulin are good introductions to these methods and provide useful algorithms. Using the least squares approach allows us to solve for the parameters k, $a_j$ and $b_j$ from the 2p+1 data points.

Time Division Multiplexing Field Generation

Referring now initially to FIG. 2, a functional diagram of an apparatus for determining position and orientation of a remote object relative to a coordinate reference frame includes a generator of electromagnetic fields, generally illustrated at 20, a remote sensor 70 and an electronic unit 100. The mode of operation, including appropriate techniques for determining position and orientation of sensor 70 in the reference coordinate frame of transmitter tablet 20, is disclosed by Mark R. Schneider in the above-referenced U.S. Pat. No. 6,073,043, and incorporated by reference. However, other techniques could be used in conjunction with the eddy current compensation disclosed herein. For example, U.S. Pat. No. 4,737,794 (Jones), U.S. Pat. No. 5,592,939 (Martinelli), U.S. Pat. No. 5,600,330 (Blood), U.S. Pat. No. 5,377,678 (Dumoulin), U.S. Pat. No. 4,710,708 (Rorden) and International Patents WO 94/04938 (Bladen) and WO 96/05768 (Ben-Haim), among others, all disclose modes of operation that could be improved with the eddy current compensation techniques disclosed herein and discussed in more detail below.

Transmitter tablet 20 includes a plurality of field generating elements such as transmitter antennas 21–28. The antennas need only be spatially and rotationally distinct such that the field generated by each antenna be distinguishable at sensor 70 and that there is a unique set of field values at all positions within the measurement volume. Antennas 21–28 are typically eight magnetic loop windings of circular or rectangular geometry, but other geometries are possible. Antennas 21–28 are supplied with time division-multiplexed ramp waveforms from current drivers 31–38. The signals are multiplexed so that the fields generated by each of the antennas are distinguishable from one another. The time division multiplexing is accomplished by demultiplexer 40, which is illustrated as a set of switches 41–48. The switches 41–48 are actuated in sequence by bussed output lines 62 of a processor 60. A digital to analog converter (DAC) 50 is driven from processor 60 to generate the analog signal that is supplied as input to drivers 31–38 in response to demultiplexer 40. It should be understood that, in the illustrated embodiment, eight current drivers, or power amplifying circuits, are provided, each being connected to one of eight field generating antennas with the demultiplexer sequentially applying an actuation signal to each of the antennas through the eight individual driving circuits. However, it will be appreciated, by those skilled in the art, that any one of a number of suitable multiplexing schemes may be employed.

Figure 3A:
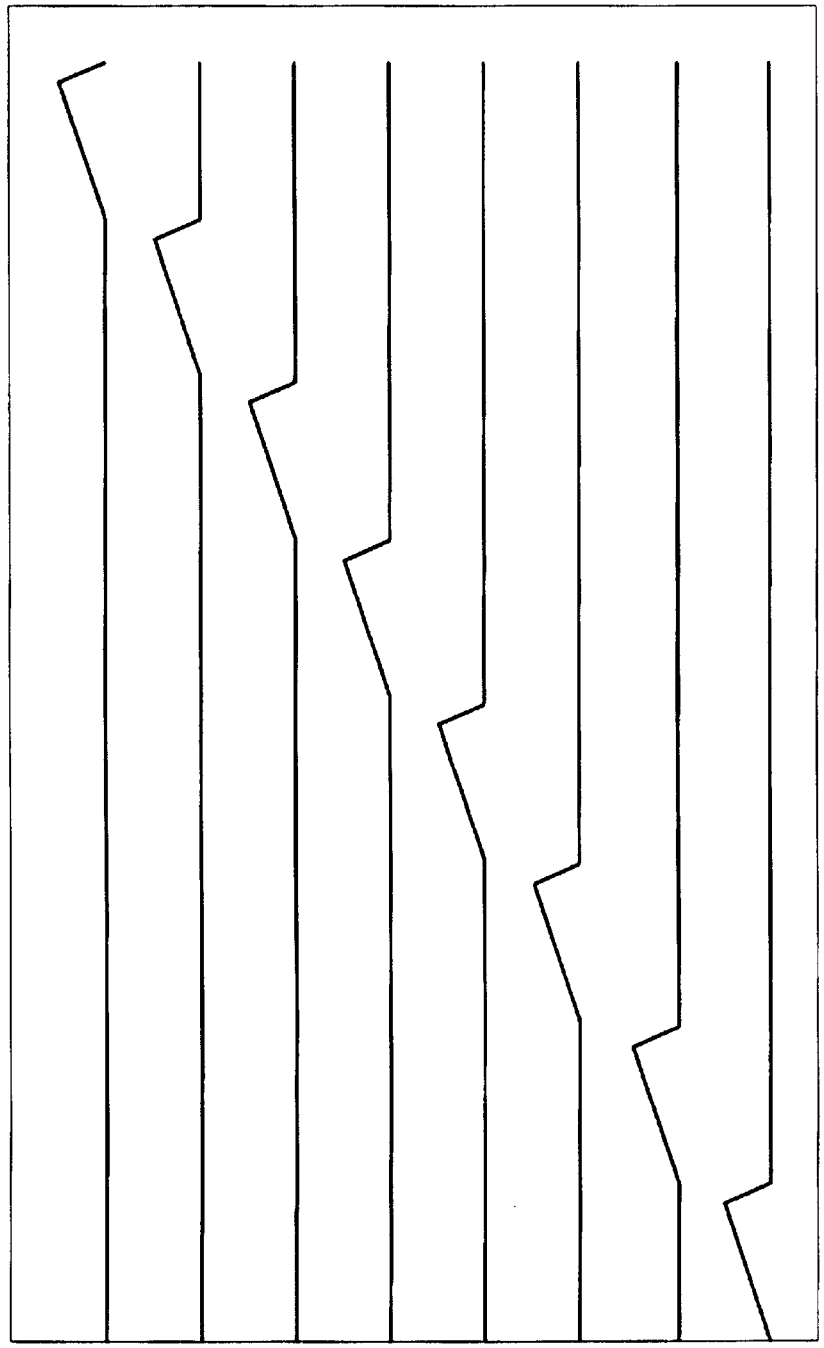

The basic system transmission cycle is illustrated in FIG. 3A in which processor 60 closes switch 41 in order to produce a ramp excitation with current driver 31 on one transmitting antenna 21 from time interval $T_1$ through $T_2$. Driver 31 is turned off by deselecting the DAC 50 by switch 41 during interval $T_2$ through $T_3$. Likewise, processor 60 closes switch 42 in order to produce a ramp excitation with current driver 32 on one transmitting antenna 22 from time interval $T_3$ through $T_4$. Driver 32 is turned off by deselecting the DAC 50 by switch 42 during interval $T_4$ through $T_5$.

Drivers 33–38 similarly provide a ramp excitation to the remaining antennas 23–28 by sequentially selecting and deselecting switches 43–48 during the remaining time periods $T_5$ through $T_{17}$. The amplitude (or slope) of the ramp produced on the eight antennas is a function of the output DAC 50 and is regulated in order to provide automatic gain control to compensate for large variations in transmitter antenna to sensor separation, as will be appreciated by those skilled in the art.

Figure 3B:
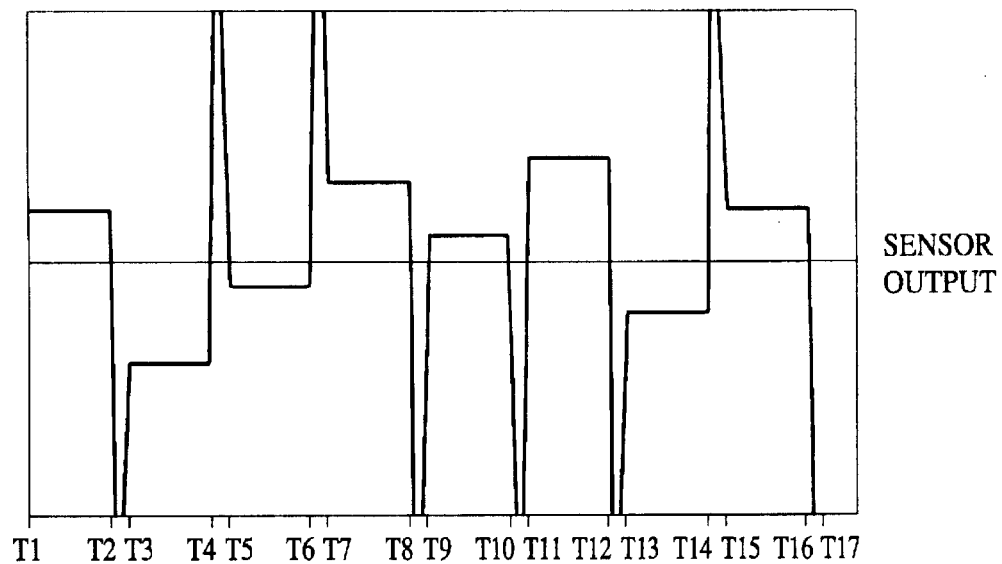
FIG. 3B is the time graph of the corresponding response of a sensor.

Sensor 70 is preferably a passive loop antenna that responds to the rate of change of magnetic field dB/dt. Sensor 70s output (FIG. 3B) is supplied to differential preamplifier 80. The output of amplifier 80 is supplied to analog to digital converter (ADC) 90 which converts the amplifier output to a discrete time digital representation for processing by processor 60. ADC 90 converts analog data fast enough to ensure that a minimum of 2p+1 data points are converted along the induced voltage curve within a time interval $T_{min}$ (to be discussed shortly). In the preferred embodiment ADC 90 converts much faster (typically 48–96 kHz) than minimally required and processor 60 adaptively picks which of the digitized points to use.

Processor 60 provides the necessary timing signals for driving demultiplexer 40, adjusting the drive amplitude of drivers 31–38 via DAC 50 and reading the data from ADC 90. Processor 60 also calculates the position and orientation of sensor 70 in a reference coordinate frame defined by transmitter tablet 20 and supplies the results to other systems via interface 61. In the illustrated embodiment the transmission sequence of ramping each of the transmitter currents to generate fields from transmitter antennas 21–28 in sequence is repeated between 10 and 50 repetitions per second. However, it should be apparent to those skilled in the art that the repetition rate could be different depending on application and that it could be adaptively regulated based on the amount of eddy current observed within the operating environment.

Figure 4:
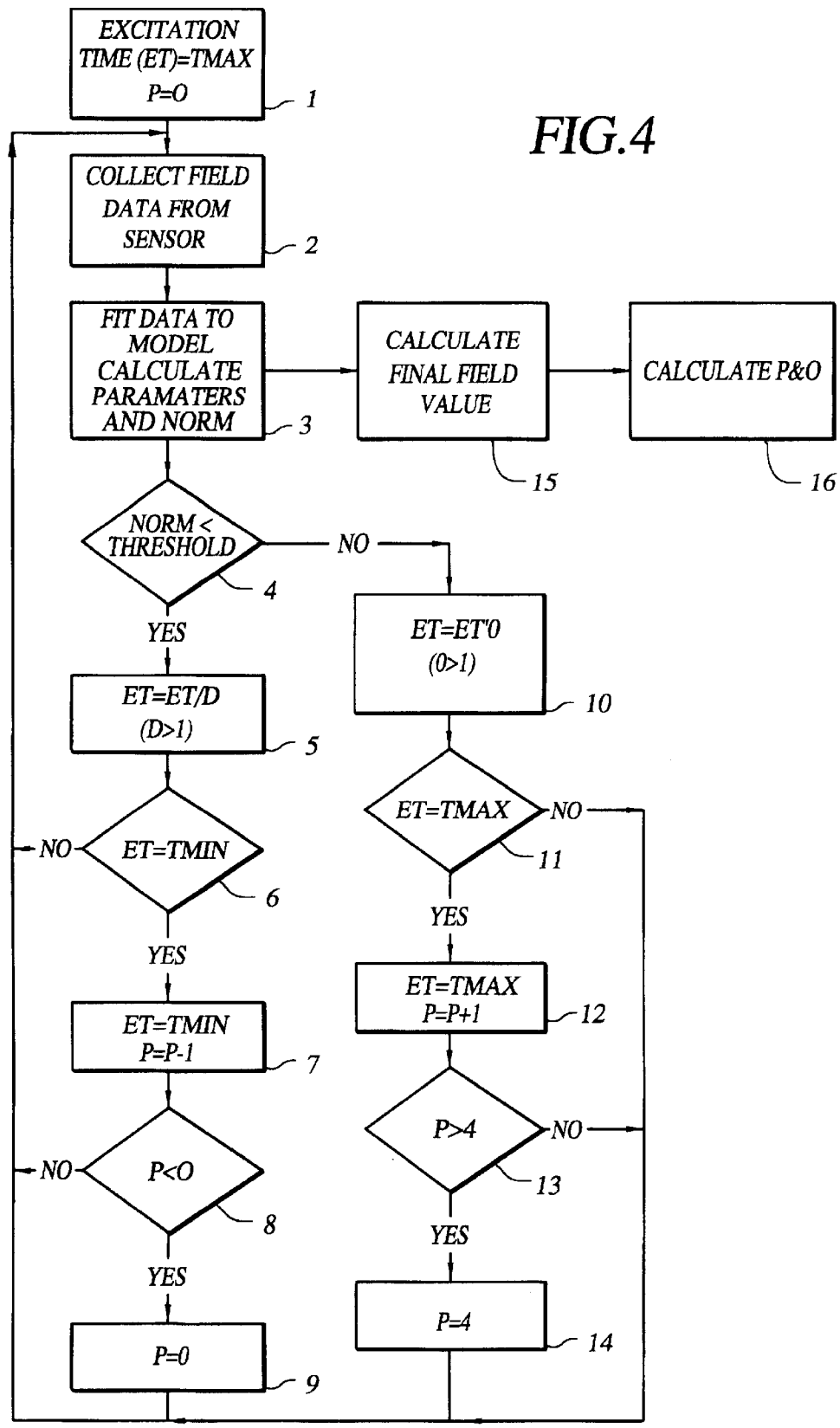
FIG. 4 is a flow chart of the technique used by the present invention to remove or greatly reduce any effects from eddy currents.

A flow chart of the processing required to remove the effects of eddy currents from the preferred embodiment in an adaptive manner is illustrated in FIG. 4. The system is first powered on. The excitation time (ET) is set to value $T_{max}$ and p is set to zero in block 1. $T_{max}$ is chosen based on two contradictory requirements: 1) it should be short enough so that the required repetition rate is acceptable; and 2) it should be long enough to provide good data to the modeling process. In the illustrated embodiment $T_{max}$ would be between 2.5 and 12.5 milliseconds. Setting p to zero tells the least squares modeling software to assume there are no eddy currents to model. In block 2 the amplified data from preamplifier 80 is collected from sensor 70 via ADC 90 during interval $T_1$ through $T_2$ (FIG. 3b), $T_3$ through $T_4$, etc., on through $T_{15}$ through $T_{16}$. Within each time interval at least 2p+1 data points are collected. In the preferred embodiment the number of data points is dependent on the rate of the conversion that ADC 90 is capable of and the values of $T_{max}$ and $T_{min}$ and is much greater than the minimum required. Processor 60 collects all the data points from ADC 90 and utilizes a subset of the data points of at least length 2p+1 to perform the modeling of the data in block 3.

How accurately the parameters k, $a_j$ and $b_j$ fit equation (4) in block 3 is measured by the norm of the residuals. The norm of the residuals is defined as the square root of the sum of the squares of the modeling function when evaluated at the determined parameters. In practice a system will produce a small but finite norm in an environment that contains no magnetic distorters (highly conductive materials). This value can be determined experimentally within a distorter free environment and would represent the threshold noted in block 4.

If the norm is less than the threshold then ET is decreased by a factor 1/d, where d is greater than one. This is denoted in block 5. In practice d would be between 1 and 2 (1<k2). ET is then tested against $T_{min}$ in block 6. If ET is not less than $T_{min}$ the process starts over at block 2 with the new ET. Otherwise no further reduction of ET is allowed (block 7) and p is decreased by 1. $T_{min}$ is chosen based on signal to noise constraints and on the requirement that 2p+1 data points must be available to the modeling process. $T_{min}$ is typically 0.5 milliseconds. Processing blocks 8 and 9 prevent the modeling technique from decreasing p below zero.

If the norm is greater than the threshold in block 4 then ET is increased by a factor d as denoted in block 10. ET is then tested against $T_{max}$ in block 11. If ET is not greater than $T_{max}$ the process starts over at block 2 with the new ET. Otherwise no further increase of ET is allowed (block 12) and p is increased by 1. This signifies that the model of the environment contains one more eddy current producer than before. Processing blocks 13 and 14 prevent the modeling technique from increasing p above four. While it is believed that p=2 would cover almost all tracking applications there is no reason not to allow p to be greater. The upper limit on p would depend mainly on the processing time for computing the model and the number of available data points that could be acquired during the time interval.

Other outputs from block 3 are the parameters k, $a_j$ and $b_j$ that best fit equation (4) in a least squares sense. These parameters are utilized to determine a final value of the waveform that would represent the value of the sensed field at infinite time and without eddy current effects. The disclosed method, unlike Bloods, provides a mathematically elegant and simple method to determine the final value of the waveform without extrapolation. This is possible due to the nature of the excitation waveform utilized in this invention. The final value theorem, applicable to Laplace transforms, is:

$$\lim_{t \to \infty} f(t) = \lim_{s \to 0} sF(s) \tag{6}$$

Applying this theorem to equations (2) and (3) yields $$\lim_{t \to \infty} v_{sensor}(t) = \lim_{s \to 0} s\left(-s\frac{c}{s^2}\left[k + \sum_{j=1}^{p} \frac{a_j}{s+b_j}\right]\right) \tag{7}$$

or $$v_{sensor}(\infty) = ck + c\sum_{j=1}^{p} \frac{a_j}{b_j} \tag{8}$$

It is seen that the value that the sampled waveform would possess at infinite time is merely a simple algebraic equation based on the calculated parameters and not a function of time. Therefore no extrapolation is necessary to determine the final value.

These final sensor values are passed to the position and orientation technique (block 16) where they are used to determine the position and orientation of sensor 70 in the reference coordinate frame of transmitter tablet 20, using a method disclosed by Mark R. Schneider in U.S. Pat. No. 6,073,043, entitled MEASURING POSITION AND ORIENTATION USING MAGNETIC FIELDS or any other applicable methods.

Other refinements to the disclosed invention will be obvious to those skilled in the art. As an example, instead of using the sampled data points from ADC 90 the sensed waveform could be integrated within processor 60. This would change the form of the equations in (3) and (4) to (9) and (10), respectively.

$$V_{sensor}(s) = -I(s)\left[k + \sum_{j=1}^{p} \frac{a_j}{s+b_j}\right] \quad (9)$$

$$v_{sensor}(t) = ckt + ct\left[\frac{a_1}{b_1} + \frac{a_2}{b_2}\right] - \frac{ca_1}{b_1}[1 - e^{-b_1 t}] - \frac{ca_2}{b_2}[1 - e^{-b_2 t}] \quad (10)$$

While integrating would improve the signal to noise ratio of the sensed signals, the final value theorem would not be able to be used. It should also be appreciated by those skilled in the art that the system could be reversed, i.e., a driver excitation could be output to a single transmitter antenna and multiple sensor antennas could simultaneously measure the field. Also, since all real measurement systems have a finite bandwidth, the system will have its own intrinsic low-pass filter response that can be characterized in terms of the $a_j$ and $b_j$ parameters. These could be measured at the time of manufacture and stored for use during normal system operation. As will also be known to those skilled in the art, excitations other than a ramp could also be used with this technique.

Frequency Division Multiplexing Field Generation Method

While time division multiplexing of the excitation waveforms is feasible, as disclosed above, frequency division multiplexing of the waveforms would yield an increase in update rate and allow multiple electromagnetic tracking systems to work near one another on a continuous basis. The following discussion will lead up to a novel method for reducing the effects of eddy currents while retaining all of the benefits of both AC and pulsed-DC electromagnetic tracking systems.

Figure 5:
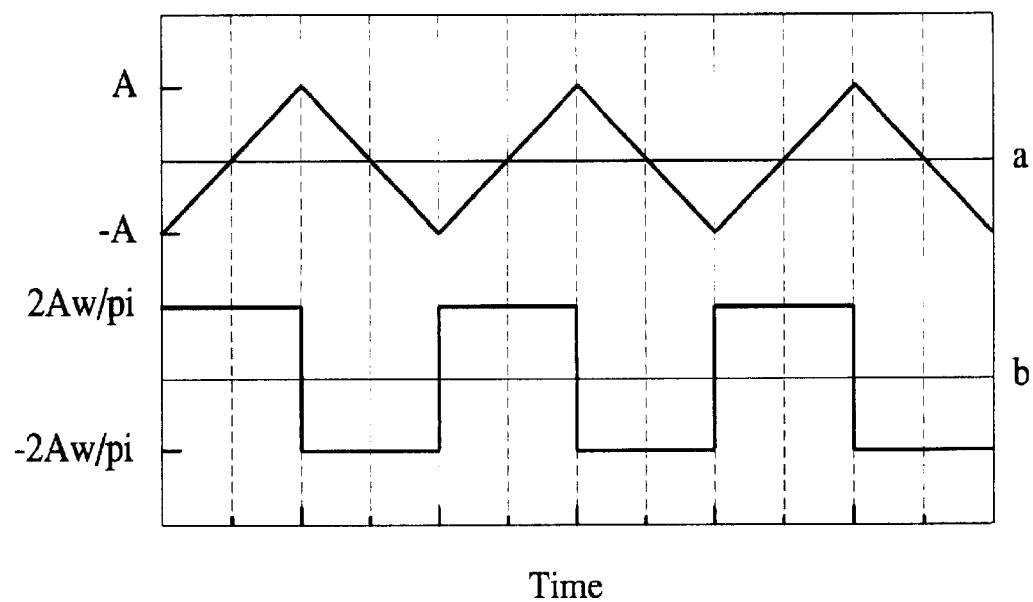
FIG. 5 is a graph showing some waveforms used with the invention.

To understand the differences between this invention and previous technologies one needs to understand the underlying physics and signal processing involved. First, the excitation waveform to the field generator is explained. This waveform is an AC waveform and is shown in FIG. 5 at line a. That it is an AC waveform can be seen by noting that the waveform can be expressed as a sum of only sinusoidal components, i.e., $$triangle(t) = \frac{-A8}{\pi^2} \sum_{q=1}^{\infty} \frac{1}{(2q-1)^2} \cos((2q-1)\omega t) \quad (11)$$

This equation is for a triangular waveform of peak amplitude A and fundamental frequency (q=1) of f=ω/2π Hz with q being an integer. Note that there are no DC terms in this expression. In an environment with no conductive materials the induced voltage has the form shown in FIG. 5 at line b. The induced voltage is a square wave, which can be expressed as:

$$square(t) = \left(\frac{2\omega}{\pi}\right)\frac{A4}{\pi} \sum_{q=1}^{\infty} \frac{1}{(2q-1)} \sin((2q-1)\omega t) \quad (12)$$

Figure 6:
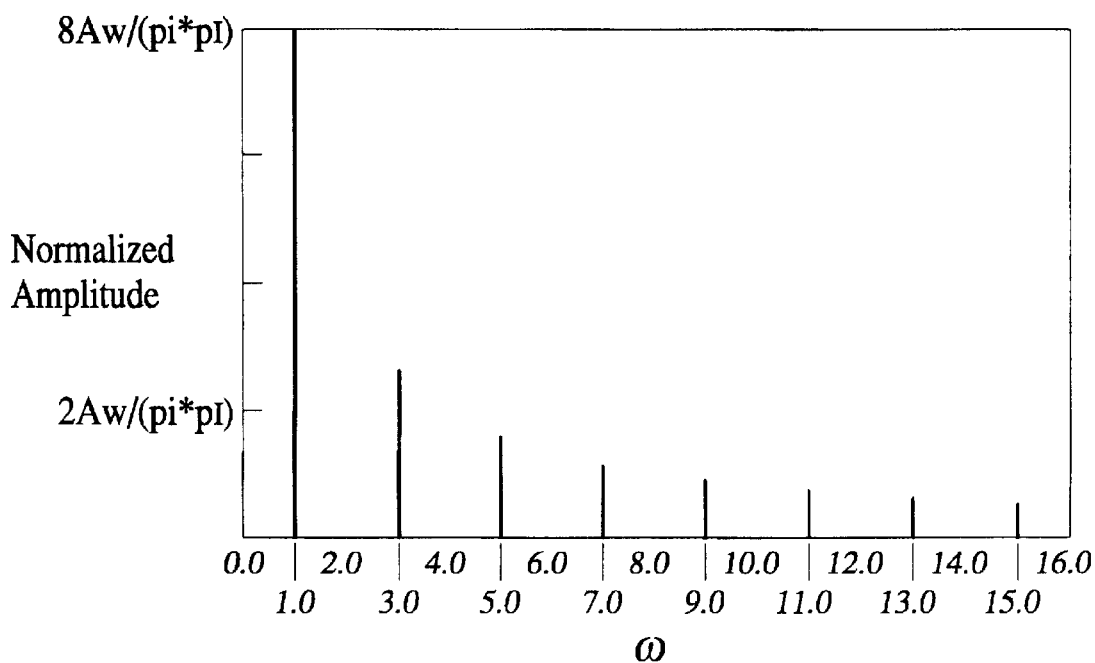
FIG. 6 is a graph showing a harmonic distribution of frequencies.

This is a direct result of applying equation (1) to equation (11). Because equation (12) is composed of only AC waveforms a DC sensitive sensor is not required (as in Blood), eliminating the problems due to the earth's magnetic field. It is obvious from equation (12) that the square wave is composed of harmonically related sinusoids whose amplitudes are inversely proportional to the $q^{th}$ harmonic of the sinusoid. Looking at this square wave in the frequency domain one would see impulses of amplitude $$\left(\frac{2\omega}{\pi}\right)\frac{A4}{\pi}\frac{1}{(2q-1)} \quad (13)$$

at frequencies (in radians) of (2q-1)w, respectively (FIG. 6).

Figure 7A:
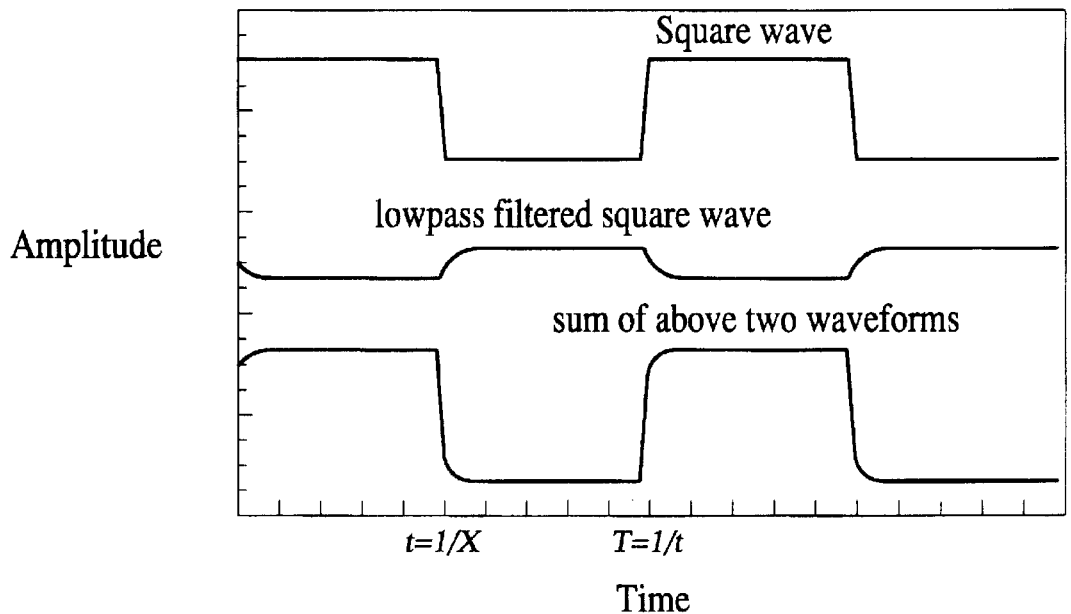

As noted previously, eddy currents induced in conductive media can be modeled by low-pass filter functions. The response of a sensor due to the field generator B-field and the B-fields due to eddy currents can be written as shown in equation (3). It is noted that equation (3), rewritten in the time domain, can be represented as the time derivative of the excitation waveform convolved with the impulse response of the magnetic coupling and the environment, or, with q=2 for example $$square(t) * |k\delta(t) + a_1 e^{-b_1 t} + a_2 e^{-b_2 t}| \quad (14)$$

where * is the convolution operator. The convolution of the square wave with the scaled (by k) delta function δ(t) is just k times the square wave. The convolution of the square wave with the scaled (by $a_j$) exponential function exp(-$b_j$t) is a low pass filtered version of the square wave scaled by $a_j$, which does not change the frequency components, only their magnitudes and phases. This is illustrated in FIG. 7A along with the summation of the waveforms. The equivalent summations in the frequency domain are shown in FIGS. 7B1, 7B2, and 7B3.

Figure 8B:
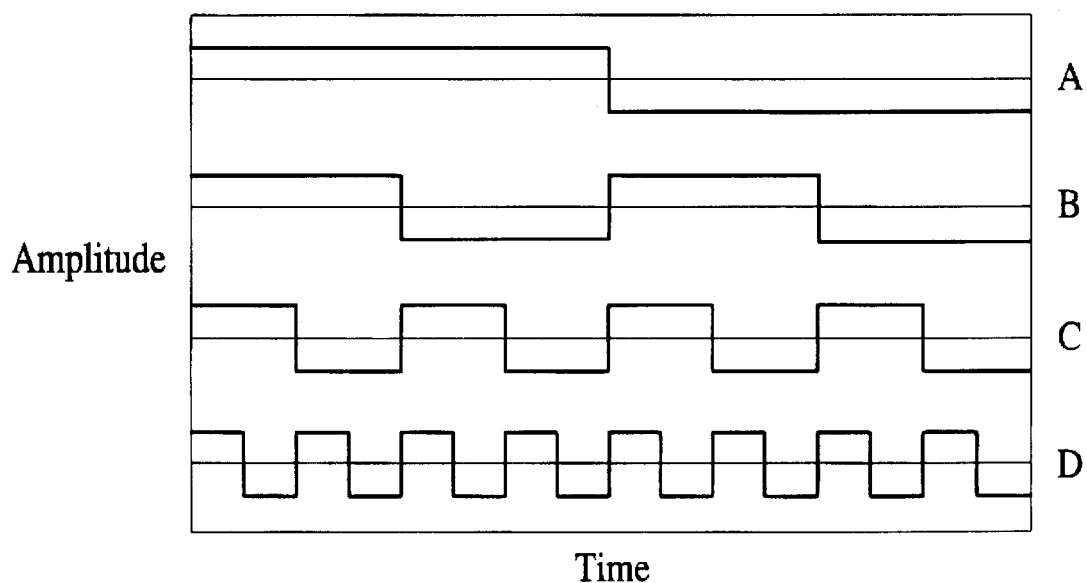
FIG. 8B shows responses to the four waveforms of FIG. 8A
Figure 8C:
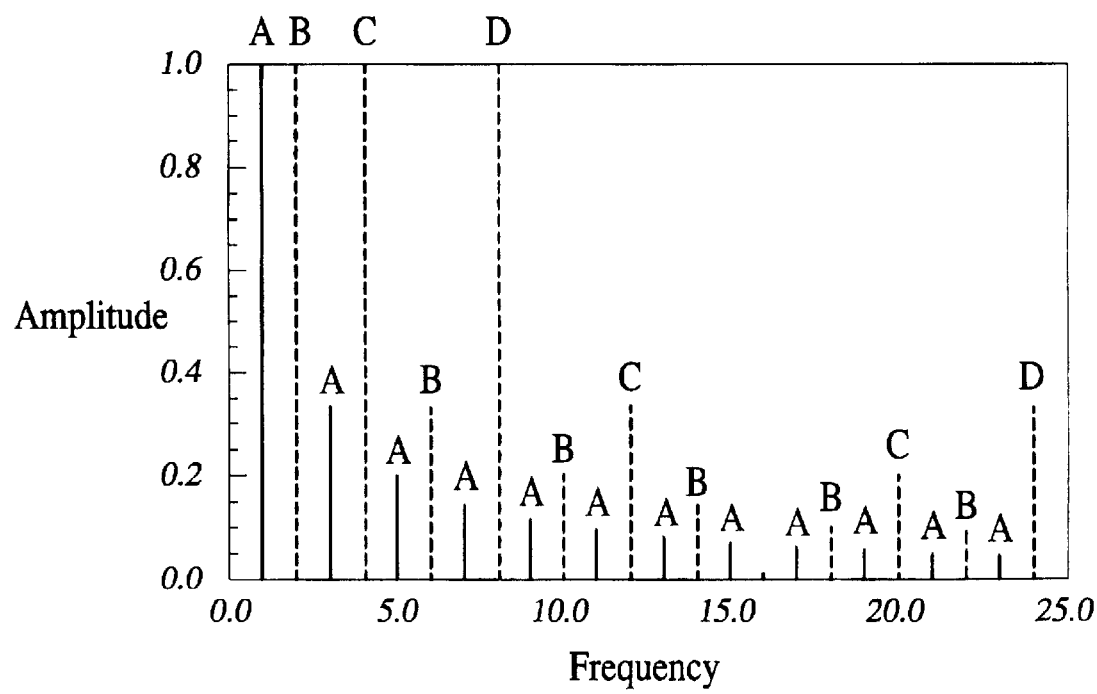
FIG. 8C shows a corresponding frequency spectra or distribution.

In order to separate the contributions from the various field generators as measured at the sensor one performs frequency division multiplexing. This means that the excitations of the field generators must be at different frequencies. By judicial choice of excitation frequencies the spectrums of the sensed square waves can be made distinct. One way to guarantee this is to have each fundamental frequency be twice the previous fundamental (alternatively, each square waves period should be half of the previous one). For example, 20, 40, 80 and 160 Hz fundamental frequency excitations (labeled A, B, C and D, respectively, in FIG. 8A) will generate waveforms shown in FIG. 8B, whose spectra do not overlap, as shown in FIG. 8C. This geometric progression of carrier frequencies, however, will not be required, as will shortly be disclosed.

Many methods exist to determine the spectra of a waveform. Coherent detection, discrete and fast Fourier transforms (DFT and FFT, respectively), sliding FFTs, chirp Z transforms, Hartley and wavelet transforms and analog and or digital filter banks all offer means to observe spectra, among others. For illustrative purposes the FFT will be used in the remaining discussions. It is known to those skilled in the art that if a signal is commensurate with the FFT sampling window (i.e., an integer number of periods of the signal fit within the window) the sampled signals spectra falls exactly within the FFTs frequency bins and contains no spectral leakage. Using this knowledge a sampling frequency can be chosen along with suitable triangle wave excitation frequencies such that:

(1) spectra from the various sensed square waveforms do not overlap, and (2) spectra fall exactly within the FFT frequency bins.

It can now be seen how to model and remove the eddy current contributions such that a more accurate field measurement can be ascertained and used in a position and orientation measurement system. A frequency domain model can be constructed, with p=2 for example, of the form $$\text{Square}(s)\left[k + \frac{a_1}{s+b_1} + \frac{a_2}{s+b_2}\right] \quad (15)$$

which is the Laplace transform of equation (14). This consists of impulses at frequencies (2q−1)w of amplitude $$\frac{1}{(2q-1)w}\left[k + \frac{a_1}{\sqrt{b_1^2 + ((2q-1)w)^2}} + \frac{a_2}{\sqrt{b_2^2 + ((2q-1)w)^2}}\right] \quad (16)$$

where w is the fundamental frequency of a square wave in radians, q is an integer, $a_j$ is proportional to the magnitude of the induced voltage due to eddy current j and is a function of range between the sensing element and the conductive material; and $b_j$ is the B3 dB corner frequency that is a characteristic of the $j^{th}$ conducting medium which is supporting the eddy current. Each square wave of fundamental frequency w will have its own associated version of equation (16). It has been found that for most practical purposes modeling the environment with two eddy currents (p=2) provides sufficient accuracy for most electromagnetic tracking applications. Of course p may be greater than or less than 2 depending on the situation, and an adaptive scheme for setting p will be disclosed.

There is no requirement to use every impulse at every frequency comprising the square wave. For example, to fit for the five parameters (k, $a_1$, $a_2$, $b_1$ and $b_2$) in equation (16) one would need only the first five harmonics of the distorted square wave. This implies that harmonic components that overlap beyond the frequencies of interest (in this case, above the fifth harmonic) are useable too. It is also not necessary to use consecutive harmonics. Thus harmonics of the prime power (50 Hz or 60 Hz) could be easily avoided. As will also be obvious to those skilled in the art, other waveforms formed from sums of sinusoids at appropriate frequencies could also be used with this technique.

Every measurement cycle a set of points is collected to be processed by the FFT technique. Using already discussed least squares methods the parameters k, $a_j$ and $b_j$ that best fit equation (16) would be determined. The value of k determined for each square wave excitation would then be used as input into the position and orientation technique. A new set of data would be collected and the process repeated indefinitely. It should be appreciated by those skilled in the art that the system could also be reversed, i.e., a triangular driver excitation of a single fundamental frequency could be output to a single transmitter antenna and multiple sensor antennas could simultaneously measure the field.

Figure 9:
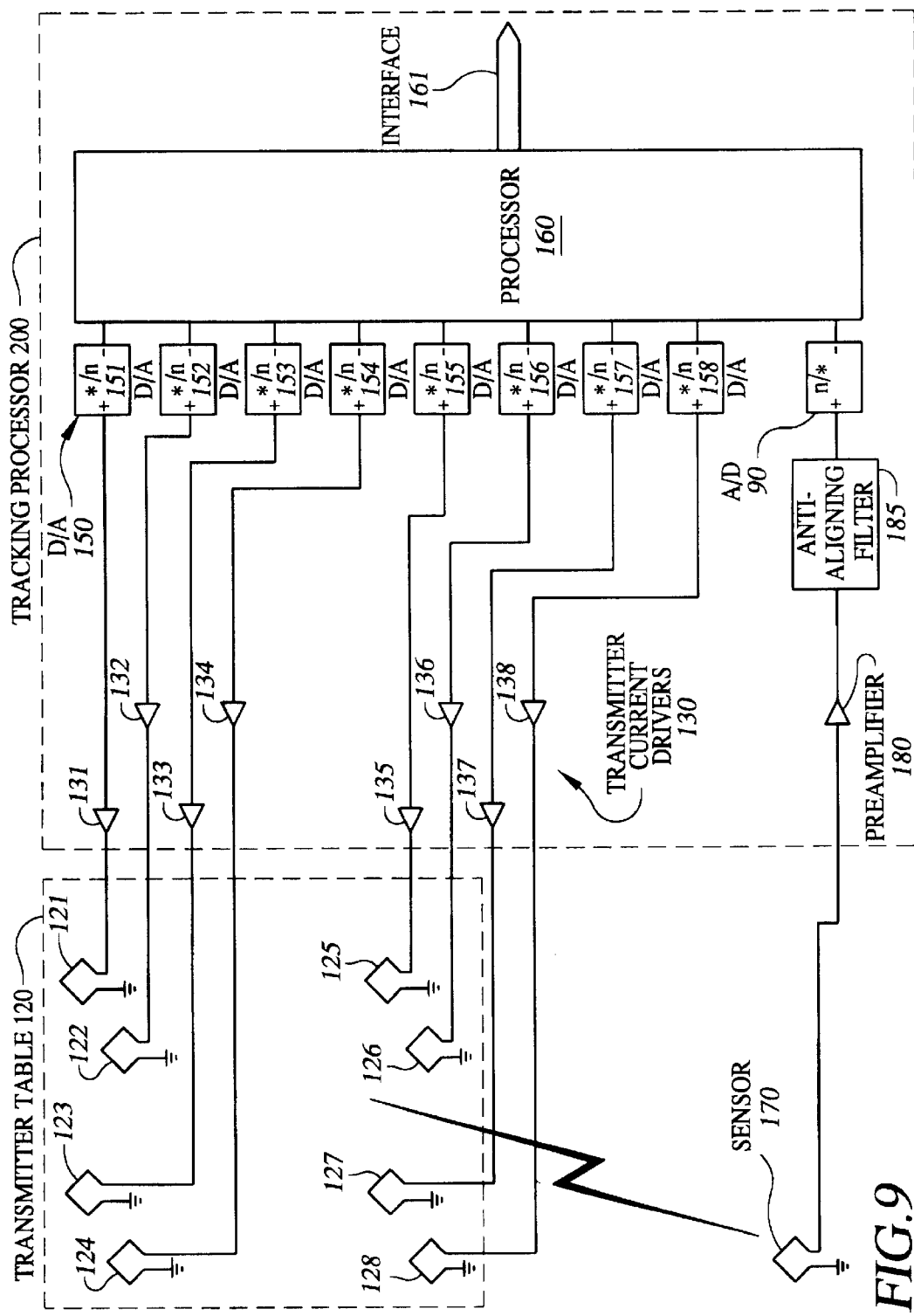
FIG. 9 is a simplified schematic of some of components of an alternate position and orientation determination system according to the present invention.

Referring now to FIG. 9, a functional diagram of an apparatus for determining position and orientation of a remote object relative to a coordinate reference frame includes a generator of electromagnetic fields, generally illustrated at 120, a remote sensor 170 and an electronic unit 200. The mode of operation, including appropriate techniques for determining position and orientation of sensor 170 in the reference coordinate frame of transmitter tablet 120, is disclosed in the present inventor's U.S. Pat. No. 6,073,043, incorporated by reference above. However, the frequency division multiplex technique of eddy compensation could be used to improve other designs such as those of U.S. Pat. No. 4,737,794 (Jones), U.S. Pat. No. 5,592,939 (Martinelli), U.S. Pat. No. 5,600,330 (Blood), U.S. Pat. No. 5,377,678 (Dumoulin), U.S. Pat. No. 4,710,708 (Rorden) and International Patents WO 94/04938 (Bladen) and WO 96/05768 (Ben-Haim), among others.

Transmitter tablet 120 includes a plurality of field generating elements such as transmitter antennas 121–128. The antennas need only be spatially and rotationally distinct such that the field generated by each antenna be distinguishable at sensor 170 and that there is a unique set of field values at all positions within the measurement volume. Antennas 121–128 are typically eight magnetic loop windings of circular or rectangular geometry, but other geometries are possible. Antennas 121–128 are supplied with AC triangular waveforms of different frequencies from current drivers 131–138. The signals are frequency division multiplexed so that the fields generated by each of the antennas is distinguishable from one another. The frequency division multiplexing is accomplished by DACs 151–158, which are driven from processor 160 to generate the analog signal that are supplied as inputs to drivers 131–138. It should be understood that, in the illustrated embodiment, eight current drivers, or power amplifying circuits, are provided, each being connected to one of eight field generating antennas with eight DACs applying actuation signals simultaneously to each of the antennas through the eight individual driving circuits.

Sensor 170 is preferably a passive loop antenna that responds to the rate of change of magnetic field dB/dt. Sensor 170s output is supplied to differential preamplifier 180. The output of amplifier 180 is supplied to anti-aliasing filter 185 which has a frequency response chosen to prevent aliasing of the sampled data while allowing suitable sensed harmonic content of the frequency division multiplexed signals to pass unaffected to ADC 190. ADC 190 converts the amplifier output to a discrete time digital representation for processing by processor 160. ADC 190 converts analog data at a rate suitable for FFT processing and chosen such that the sampled signals spectra falls exactly within the FFTs frequency bins and contains no spectral leakage. In the preferred processor 160 adaptively picks which of the excitation waveforms harmonics to use.

Processor 160 provides the necessary timing signals for driving DACs 151–158 and reading the data from ADC 190. Processor 160 also calculates the position and orientation of sensor 170 in a reference coordinate frame defined by transmitter tablet 120 and supplies the results to other systems via interface 161. In the illustrated embodiment the triangular AC excitation frequencies are below 2 kHz. However, it should be apparent to those skilled in the art that the frequencies could be different depending on application and the operating environment. It should also be obvious to those skilled in the art that other waveforms formed from sums of sinusoids of appropriate frequencies could also be used with this technique.

Figure 10:
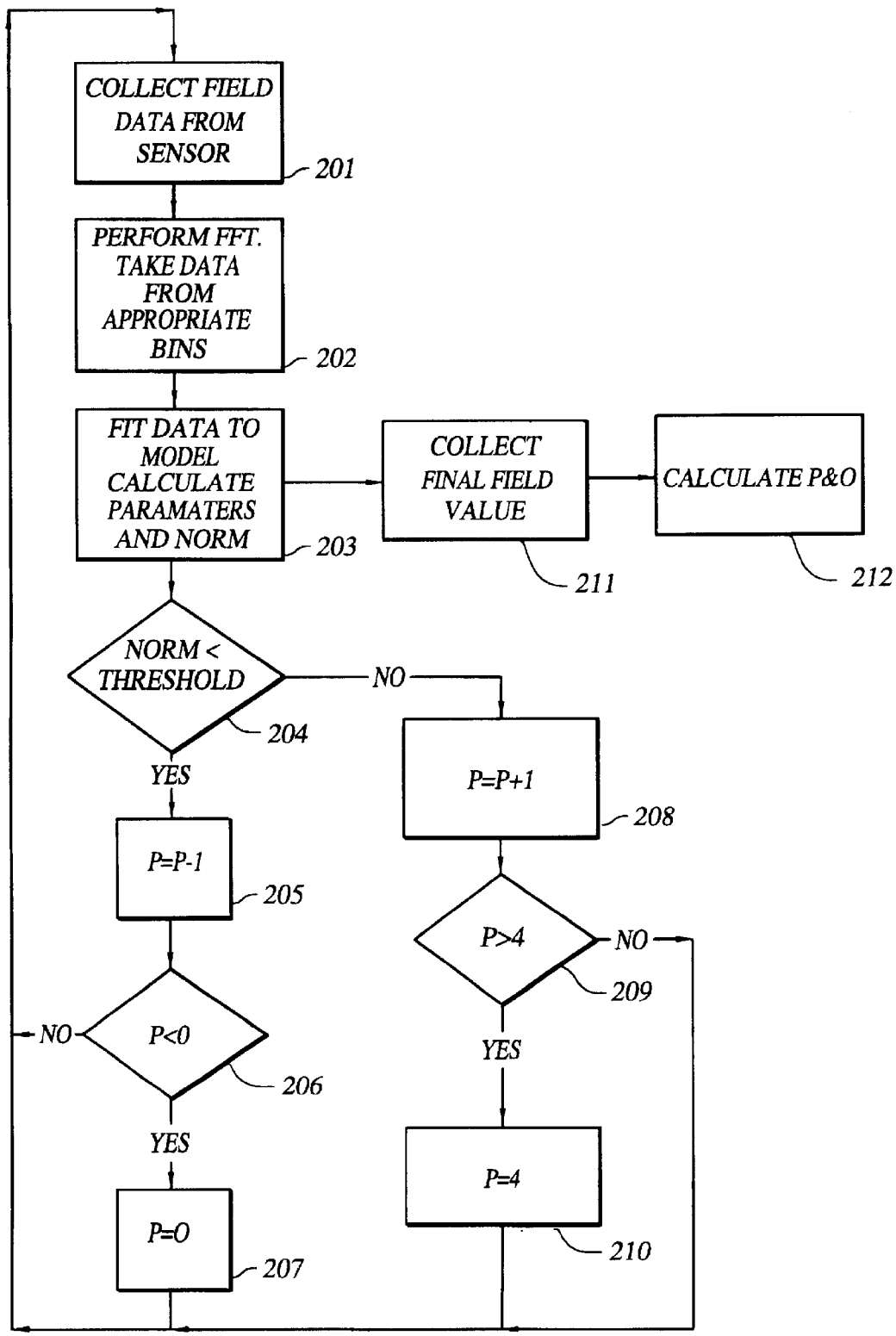
FIG. 10 is a flow chart of the technique used by the FIG. 9 system.

A flow chart of the processing required to remove the effects of eddy currents from the preferred embodiment in an adaptive manner is illustrated in FIG. 10. The system is first powered on. In 201 the sensors (170) data is amplified by preamplifier 180, filtered by anti-aliasing filter 185 and collected via ADC 190 and p is set to zero. Setting p to zero tells the least squares modeling software to assume there are no eddy currents to model. In the preferred embodiment the number of data points is dependent on the rate of data conversion of the ADC 190 as well as its suitability for FFT processing. The rate is chosen such that the sampled signals spectra falls exactly within the FFTs frequency bins and contains no spectral leakage. Processor 160 collects all the data points from ADC 190, performs an FFT on the data and utilizes the harmonics to perform the modeling of the data in 203.

How accurately the parameters k, $a_j$ and $b_j$ fit equation (16) is measured by the norm of the residuals. The norm of the residuals is defined as the square root of the sum of the squares of the modeling function when evaluated at the determined parameters. In practice a system will produce a small but finite norm in an environment that contains no magnetic distorters (highly conductive materials). This value can be determined experimentally within a distorter free environment and would represent the threshold noted in block 204.

If the norm is less than the threshold then p is decreased by one in block 205, signifying that there is one less distorter to model. Processing blocks 206 and 207 prevent the modeling technique from decreasing p below zero. If the norm is greater than the threshold in block 204 then p is increased by 1. This signifies that the model of the environment contains one more eddy current producer than before. Processing blocks 209 and 210 prevent the modeling technique from increasing p above four. While it is believed that p=2 would cover almost all tracking applications there is no reason not to allow p to be greater. The upper limit on p would depend mainly on the processing time for computing the model.

Other outputs from block 203 are the parameters k, $a_j$ and $b_j$ that best fit equation (16) in a least squares sense. These parameters are utilized to determine a final value of the waveform that would represent the value of the sensed field without eddy current effects.

It should be appreciated by those skilled in the art that the system could be reversed, i.e., a driver excitation could be output to a single transmitter antenna and multiple sensor antennas could simultaneously measure the field. Also, since all real measurement systems have a finite bandwidth, the system will have its own intrinsic low-pass filter response that can be characterized in terms of the $a_j$ and $b_j$ parameters. These could be measured at the time of manufacture and stored for use during normal system operation.

The remote object position and orientation determining system of the present invention has a wide variety of applications. For example, sensor 70 or 170 can be placed at the end of a catheter or flexible endoscope for tracking the path of travel or the location of the catheter tip. This is especially useful in cardiac applications, e.g., for the treatment of cardiac arrhythmias, drug delivery and biopsy needle placement. Another use for sensor 70 or 170 is to embed the sensor into a contact lens for eye tracking. The eye tracking could also facilitate laser eye surgery by adjusting the aim of the laser during eye movements. Another application would place numerous sensors 70 or 170 around the fingers to provide a measure of finger movement for evaluating rehabilitation progress or as part of a virtual reality data glove, a device that allow hand movement to be translated into a virtual environment. Sensor 70 or 170 can also be associated with the stylus of a three dimensional digitizer which is used to trace a physical model or the like and generate a digital database. The resulting database can then be used to generate a wide variety of computer generated images of the physical model. It should also be obvious that a 2 dimensional digitizer can be constructed using this technology. Still another application would be as a stylus input for a Personal Digital Assistant (PDA). Still another application would be gait analysis where multiple sensors 70 or 170 could be placed on various points on the body. The alignment of joints in arthroplasty procedures is another application that could be drastically improved by measuring the position and orientation of bone alignment before and during the procedure.

Multiple sensors 70 or 170 can be used for forming three-dimensional echocardiograms by tracking a handheld ultrasound scanner head. In still another application, multiple sensors 70 or 170 can be associated with a particular body part for the purpose of conducting biomechanical studies. Still another application involves the monitoring of the body movements of an invalid for the purpose of creating a nonverbal communication system or providing a technique for remotely controlling various devices with nonverbal communicative body motion. Another application is the tracking of head movements for use in virtual reality headsets. Still another application is a 3 dimensional mouse for navigating in multidimensional databases or as a tool for use with VRML, a 3 dimensional file format popular on the Internet.

Splines

Another method to improve the operation of a position and orientation determination system will use a spline technique for greater accuracy. Some explanation of splines is appropriate before describing how usage of splines can improve the operation of a position and orientation determination system.

Fitting data to splines is an interpolation method that utilizes piecewise approximations by polynomials of degree n on an interval. They are fitted to the function at specified points (nodes or knots) where the polynomial used can change but the derivatives of the polynomials are required to match up to degree n−1 at each side of the nodes. A good reference is de Boor, C. 1978, "A Practical Guide to Splines".

In the present usage, the magnetic fields from the field generating coils are measured at known positions and in the three Cartesian coordinate unit vector directions $a_x$, $a_y$ and $a_z$. Basically, data is gathered for each coil and each direction. Instead of performing a calculation of what the magnetic field should be for a given generator coil position and orientation and a given sensor position based on the equations defining the magnetic fields (the model method), the spline technique measures the magnetic fields for numerous possibilities and effectively stores a three dimensional piecewise polynomial representing the actual fields such that later measurements (such as when a catheter or other device is in use) can use the polynomial mapping of magnetic fields to determine the position and orientation.

A three-dimensional curve fit (the splines) is performed on the collected data for each coil and, for each coil, for each direction. In the preferred embodiments discussed above, that's 8 coils and 3 orientations for a total of 24 separate spline fits. When one enters the spline with a point: {x,y,z}, the spline returns a magnetic field value for that point for that particular direction, interpolating between the collected data. The data collection grid size, the order of the spline (linear, quadratic, cubic, etc.) and the features of the spline (tensor, exponential, rational, etc.) determine how well and in what manner the spline interpolates. Other mathematical conditions can also be included into the splines including the requirement that the divergence of the three dimensional magnetic field equals zero at every point. This is one of Maxwell's equations and states that magnetic flux is always found in closed loops and never diverges from a point source. This condition forces the spline interpolation to agree with magnetic field theory. The present embodiment does not extrapolate beyond the sampled magnetic field data region, but conversion of the splines into a different representation (see de Boor, op cit, and Renska, R. J., "Interpolatory Tension Splines with Automatic Selection of Tension Factors," SIAM Journal Sci. Stat. Comput., volume 8, number 3, May 1987, pps393–415) permits that. The de Boor book and Renska article are hereby incorporated by reference in their entireties.

An advantage of the spline method is that it uses the actual sensed magnetic field. This allows all manner of magnetic field generating coil designs including, for example, Helmholtz (U.S. Pat. No. 5,558,091, Acker), overlapped and stacked (U.S. Pat. No. 5,752,513, Acker), multi-axis (U.S. Pat. No. 4,737,794, Jones; U.S. Pat. No. 4,742,356, Kuipers; U.S. Pat. No. 5,600,330, Blood; WO 94/04938, Bladen, among others), planar grids (U.S. Pat. No. 5,429,132, Guy), rotating magnets, current sheets, approximations to current sheets, spirals and any other magnetic field generation scheme. It is also possible to use splines to map the Earth's magnetic field, if so desired.

The spline technique is also a method that corrects for errors in the hardware, including fixed circuit distortions, non-linearity, cross-coupling, drift, etc. It will also correct for magnetic distortions due to conductive and magnetic materials that remain fixed in the environment.

In the preferred embodiment, the magnetic field data is collected along with the current waveform excitations through the magnetic field generating coils. The magnetic field data is then normalized by dividing the collected magnetic field data by the appropriate excitation current. This normalized data is then used to generate the splines. To use the splines in the position and orientation tracking algorithm one uses the value that is returned when one enters the spline with a point: $\{x,y,z\}$. This value is then de-normalized by multiplying it by the present excitation current. This corrects for changes in the excitation due to component drift or manufacturing tolerances and allows for interchangeability of components, for example.

To solve for position and orientation one needs to solve functions of the form:

$$\lambda_p[\vec{B}_x, \vec{B}_y, \vec{B}_z]_p \cdot \lambda_q [\cos\alpha \cdot \bar{a}_x, \cos\beta \cdot \bar{a}_y, \cos\gamma \cdot \bar{a}_z]_q - v_{p,q} = 0 \quad (17)$$

where $B_x$, $B_y$ and $B_z$, are the x, y and z splines of the $p^{th}$ generating coil's magnetic field; $a_x$, $a_y$ and $a_z$ are unit vectors in the direction of the Cartesian coordinate axes; $\cos\alpha$, $\cos\beta$ and $\cos\gamma$ are direction cosines of sensor coil q; $\lambda_q$ is the effective area of sensing coil q; $\lambda_p$ represents the de-normalized excitation current of the $p^{th}$ generating coil; and $v_{p,q}$ is the induced voltage at sensing coil q for the $p^{th}$ generating coil. The unknowns are the x, y and z position of the sensing coil and the 3q direction cosines. For 1 sensing coil q=1.

There are a number of iterative methods for solving this set of non-linear equations problem. Both the non-linear systems of equations problem and the non-linear least squares problem are applicable. The non-linear systems of equations problem is: given n functions $f_1, f_2, \ldots, f_n$ of the n variables $x_1, x_2, \ldots, x_n$ find values for $x_1, x_2, \ldots, x_n$ that solve the non-linear system of equations $$f_i(x_1, x_2, \ldots, x_n) = 0, \ 1 \leq i \leq n \quad (18)$$

The non-linear least squares problem is: given m functions $f_1, f_2 \ldots, f_m$ of the n variables $x_1, x_2, \ldots, x_n$, with $m \geq n$, find values for $x_1, x_2, \ldots, x_n$ that solve the non-linear least squares problem $$\min\left\{\sum_{i=1}^{m} f_i(x)^2 : x \in R^n\right\} \quad (19)$$

Many methods exist to tackling these problems with the predominant methods requiring the evaluation of the Jacobian (a matrix of partial derivatives of the equations with respect to the unknowns), either explicitly or by finite differences and sometimes requiring the evaluation of the Hessian (a matrix of second partial derivatives of the equations with respect to the unknowns). These methods are often referred to as Newton methods, gradient methods or steepest descent methods or variations on that theme. These methods are the ones that have been noted in Hansen (U.S. Pat. Nos. 4,622,644, 4,642,786), Rorden et al. (U.S. Pat. No. 4,710,708), Dumoulin et al. (U.S. Pat. No. 5,377,678) Acker (U.S. Pat. No. 5,752,513) and Blood (U.S. Pat. No. 5,600, 330). Other methods are discussed by Mark R. Schneider in [a co-pending application]U.S. Pat. No. 6,073,043, entitled MEASURING POSITION AND ORIENTATION USING MAGNETIC FIELDS.

An advantage of splines over other curve fitting methods is that their order determines the continuity of their derivatives and that the derivatives are easily calculated. This is especially useful in the solution of systems of non-linear equations (as noted above) where knowing the Jacobian or Hessian of the splines improves accuracy and convergence speed of the algorithm.

There are many other ways in which splines can be used to improve overall performance of magnetic tracking systems. Instead of collecting data over an entire volume for multiple field generators a spline fit of the magnetic field generated by one field generating coil could be performed and used as a prototype model, as in the present inventor's previously incorporated patent application. (This assumes that the coils are similar enough geometrically). Another use of splines would be in correcting field generating models. Ben-Haim (WO 96/05768) and Jones (U.S. Pat. No. 5,307, 072) both use Legendre polynomials to correct their simple dipole model of a field generator. Splines could be used in place of the Legendre polynomials. Since many techniques use some form of approximation, the spline techniques could be used to fit the remaining errors in the model.

Still another feature of splines that would improve magnetic tracking systems is the ability to use measured magnetic field data that does not come from a regular grid. Certain formulations of the splines allow for this (Spath, H., "Two Dimensional Spline Interpolation Algorithms," 1995). A better spline fit can be achieved by taking data in regions where the magnetic field measurements change rapidly. This would be most useful close to magnetic field generators or in heavily distorted environments. Another variation on this concept would be to fit different regions with different sets of splines.

Still another feature of splines that would improve magnetic tracking systems is "re-gridding." In the present embodiment, the order of the spline is typically 3 or 4 (a quadratic or cubic fit, respectively) and the grid spacing is between 10 mm and 40 mm. Spline evaluation slows down as the order goes up so that the fastest evaluation occurs when the spline order is 2 (a linear fit); this of course directly relates to tracking system responsiveness. The re-gridding process first generates a cubic fit of the data. These cubic splines are then re-evaluated on a finer grid, typically 1 mm to 10 mm. This data is then used to generate new splines of order 2 which are used in the tracking algorithm.

Up to now it has been assumed that the splines were fit to the field data and that the splines were saved in computer memory (in place of magnetic field models) for use in determining position and orientation. However, there is nothing that requires that the magnetic field data be first fit to splines and then the splines saved. The splines can be fit to data on the fly, calculating the splines only as required (as the sensor moves through the mapped data). This would require fitting the data within a small volume around the expected solution. With a dense enough grid of data the splines could perform a linear interpolation (a spline of order 2). It will be obvious to those skilled in the art that there are many other ways to use splines. It should also be obvious that any curve, surface, volumetric or parametric mathematical function that fits the collected magnetic field data well enough can be used. This includes polynomials, rational functions, trigonometric functions and Fourier functions, among others. Also obvious is that interchanging the transmitting and receiving coils is viable, 6DOF systems where there are 3 transmitting coils and 2 or 3 receiving coils is viable, non-coil receiving means are viable, re-transmission schemes such as those disclosed by Hansen (U.S. Pat. No. 4,642,786) and Gilboa (WO 98/36236), among others, are viable and DC excitations are viable. The spline technique can also be applied to other types of tracking systems such as those that use electric fields, sound or ultrasound waves, light or nuclear decay.

Figure 11A:
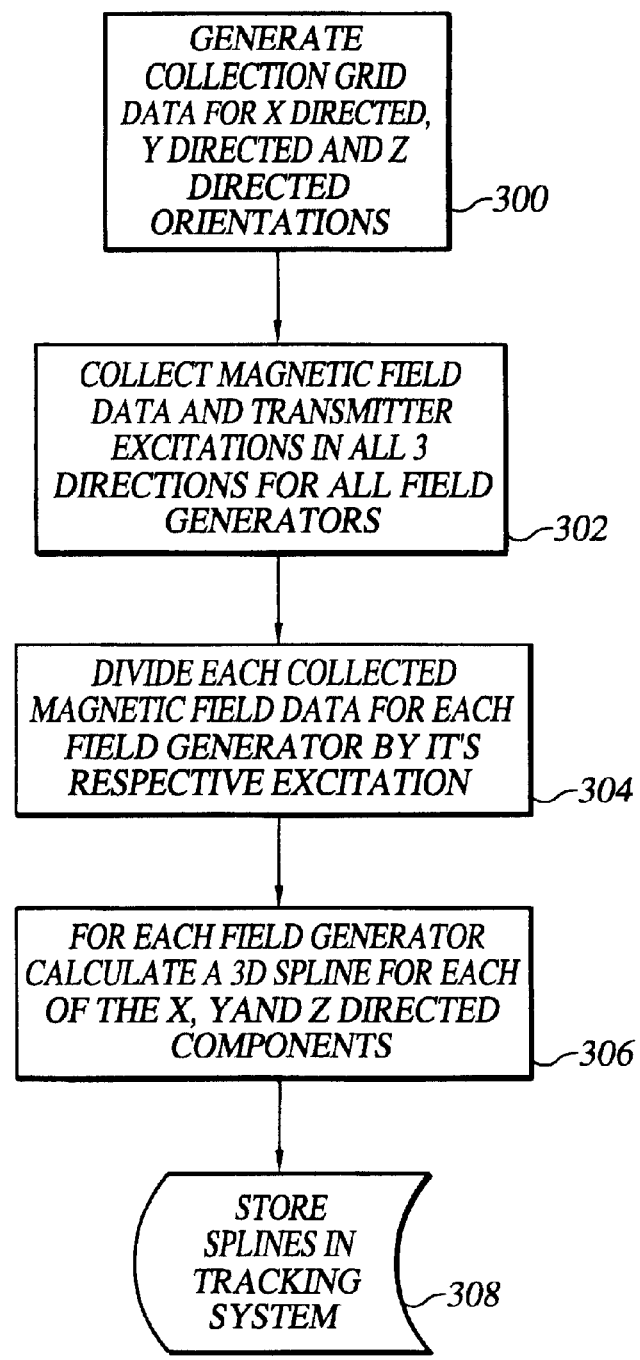
FIGS. 11A and 11B are simplified flowcharts of a technique for using splines in the position and orientation system.
Figure 11B:
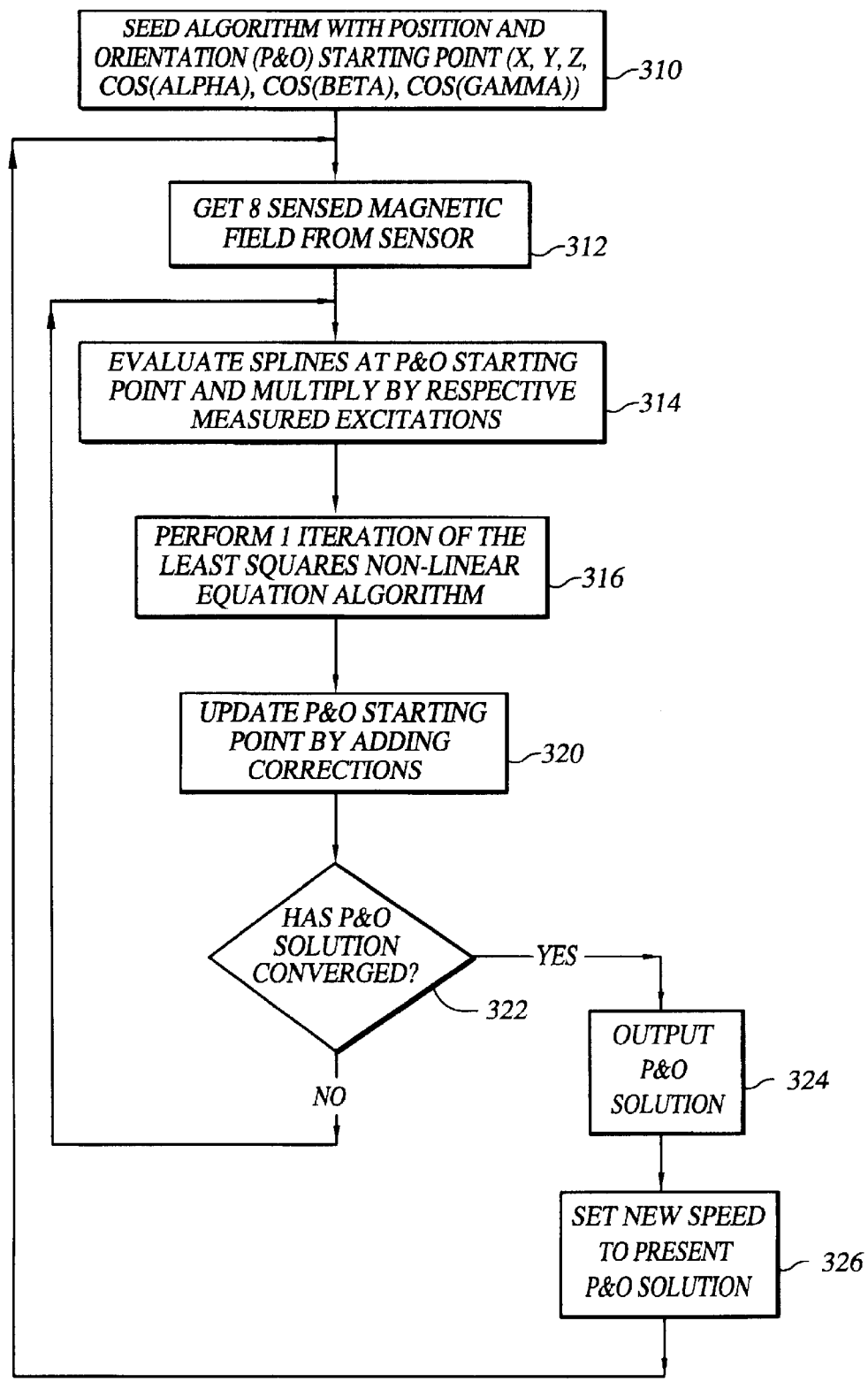

FIGS. 11A and 11B are simplified flowcharts of a technique for using splines in the position and orientation system. FIG. 11A flowcharts the mechanism for collection of the magnetic field data and its conversion into splines. In block 300 the grid for data collection is generated. It is designed to cover the volume where the magnetic tracking system is to work. This data would typically be used by a motion platform capable of translating the sensing device within the tracking volume. A single or multiple axis sensing device can be used to collect the magnetic field data. The motion platform must be able to accommodate rotations to the three Cartesian coordinate axes if a single axis sensing device is used. This same grid would typically be used during spline generation, but this is not necessary. In block 302 the motion platform moves the sensing device throughout the tracking volume, collecting magnetic field data from the 8 magnetic field generators at the previously defined grid. During this time the excitations delivered to the 8 field generators are also recorded. In block 304 the collected magnetic field data from the 8 field generators is divided by their respective excitation levels on a point by point basis. Block 306 takes the scaled magnetic field data from block 304 and the collection grid from block 300 and generates 24 splines, i.e., 8 sets of 3 splines each. Each set is for a particular field generator and each spline in the set is for a particular orientation. In block 308 the splines generated from block 306 are saved into a magnetic tracking system. This can be saved in any form of non-volatile memory.

FIG. 11B flowcharts the mechanism for using the splines within a magnetic tracking system. In block 310 an initial starting point for the position and orientation algorithm is chosen. Methods to perform this operation are disclosed by Mark R. Schneider in U.S. Pat. No. 6,073,043, entitled MEASURING POSITION AND ORIENTATION USING MAGNETIC FIELDS or any other applicable methods. Block 312 obtains the sensed magnetic fields from the sensor due to the 8 field generators. This signal conditioning process is detailed in the aforementioned patent. Blocks 314–322 form the basis of the nonlinear equation solver based on the method of least squares. In block 314 the 8 sets of splines are scaled by the most recently measured field generator excitation levels and then evaluated at the position and orientation starting point. This yields a predicted set of magnetic field readings. In block 316 the difference the difference between the sensed magnetic fields and the predicted values drives the least squares algorithm to make a correction to the starting point. This is indicated by block 320. The correction is in a direction intended to reduce the square root of the sum of the squares of the differences between the sensed magnetic fields and the predicted values. Block 322 decides whether the corrected position and orientation satisfies certain convergence criteria, indicating the solution has been reached. If the solution has not been reached then the corrected starting point becomes the new starting point and the process repeats through blocks 314–320 until convergence is achieved.

When convergence occurs the value of the position and orientation solution that caused convergence is output. This output then becomes the new seed position and orientation in block 326 and the entire process starts over at block 312.

Automatic Calibration

Another method to improve the operation of a magnetic position and orientation determination system provides a means of determining the sensor coil gain without requiring special mechanical fixturing, helmholtz coils or requiring the sensor to be placed at a known position and/or orientation. This eliminates the need for having a memory device containing the sensors gain (as determined during manufacture) or for having a very tight tolerance on the sensor gain.

The tracking problem formulation can be stated, as before, as:

$$\lambda_p[\vec{B}_x, \vec{B}_y, \vec{B}_z]_p \cdot \lambda_q [\cos\alpha \cdot \vec{i}, \cos\beta \cdot \vec{j}, \cos\gamma \cdot \vec{k}]_q - v_{p,q} = 0$$

where $B_x$, $B_y$ and $B_z$ are the x, y and z components of the $p^{th}$ generating coil's B field; i, j and k are unit vectors in the direction of the Cartesian coordinate axes; $\cos\alpha$, $\cos\beta$ and $\cos\gamma$ are direction cosines of sensor coil q; $\lambda_q$ is the effective area of sensing coil q; $\lambda_p$ represents the number of turns comprising the $p^{th}$ generating coil and, for sinusoidally varying currents, a term proportional to frequency; and $v_{p,q}$ is the induced voltage at sensing coil q for the $p^{th}$ generating coil. The unknowns are the x, y and z position of the sensing coil and the 3q direction cosines. For 1 sensing coil q=1. This formulation is also true of the spline formulation, where $B_x$, $B_y$ and $B_z$ are determined by spline functions and the p subscript represents the de-normalized excitation current of the $p^{th}$ generating coil. Implicit in the induced voltage $v_{p,q}$ term is the sensor area. Sensor area is proportional to the area of the coil times the number of turns (for a coil).

Tracking systems that use a least squares minimization technique (such as the techniques previously discussed) can simply modify the set of equations to the following form:

$$\lambda_p[\vec{B}_x, \vec{B}_y, \vec{B}_z]_p \cdot \lambda_q [\cos\alpha \cdot \vec{i}, \cos\beta \cdot \vec{j}, \cos\gamma \cdot \vec{k}]_q - v_{p,q} \cdot h = 0$$

where h represents the ratio of the assumed sensor gain to the true sensor gain. The unknowns are now the x, y and z position of the sensing coil the 3q direction cosines and the factor h. Solving additionally for the h that minimizes the above equation removes any common gain errors in the electronics due to interchanging of sensor coils, electronic components or other manufacturing tolerances. One must still have the number of equations greater then or equal to the number of unknowns.

The other benefit to automatic calibration is with systems that use AGC (automatic gain control). AGC is a method of increasing the dynamic range of a signal, thus enabling a magnetic tracking system to achieve greater range. This can be done at the field generating end by varying the excitation amplitude or at the sensing end by varying the amplification. Electromagnetic tracking systems that use AGC are disclosed by Egli (U.S. Pat. No. 4,394,831), Constant (U.S. Pat. No. 4,396,885), Blood (U.S. Pat. Nos. 4,613,866, 4,849,692, 4,945,395 and 5,600,330), Jones (U.S. Pat. No. 4,737,794 and 5,307,072), Kuipers (U.S. Pat. No. 4,742,356), Rotier (U.S. Pat. No. 4,829,250), Anderson (U.S. Pat. Nos. 5,453,686 and 5,640,170), among others. These systems need to have very accurate and known AGC stages so that the applied AGC can be backed out of the magnetic field measurements.

In the present embodiment automatic calibration works on the sensing end by applying a software gain instead of adjusting the amplitude of the sensed magnetic fields. This eliminates the need for manufacturing sensing devices with identical gains or characterizing the gains after manufacture, which facilitates their use in disposable products. This also corrects for variations in the amplifiers and other signal processing stages following the sensing devices due to drift and component tolerances. This technique can also be applied to the magnetic field generating portion of a magnetic tracking system. For either case the number of equations must equal or exceed the number of unknown variables solved for.

When using the spline technique with automatic calibration it is still required to collect magnetic field data accurately, whether there is AGC circuitry or not. However, this is only required of the system that collects the data (this is true of the model method too). Once the data has been converted into splines it can be used by other systems and sensing devices with different front end gains.

Another way to perform sensor calibration is based on Dumoulin (U.S. Pat. No. 5,377,678). The sensing device can be placed at a known position, known orientation, or both. With this known, fixed data, equation (19) can be solved for the sensing gain h. Another way to perform automatic calibration is to perform one calculation of equation (18), solve for position and orientation, use that position and orientation solution as a fixed reference, and perform one calculation of equation (19) to solve for h. This process can be iterated as necessary.

Figure 12:
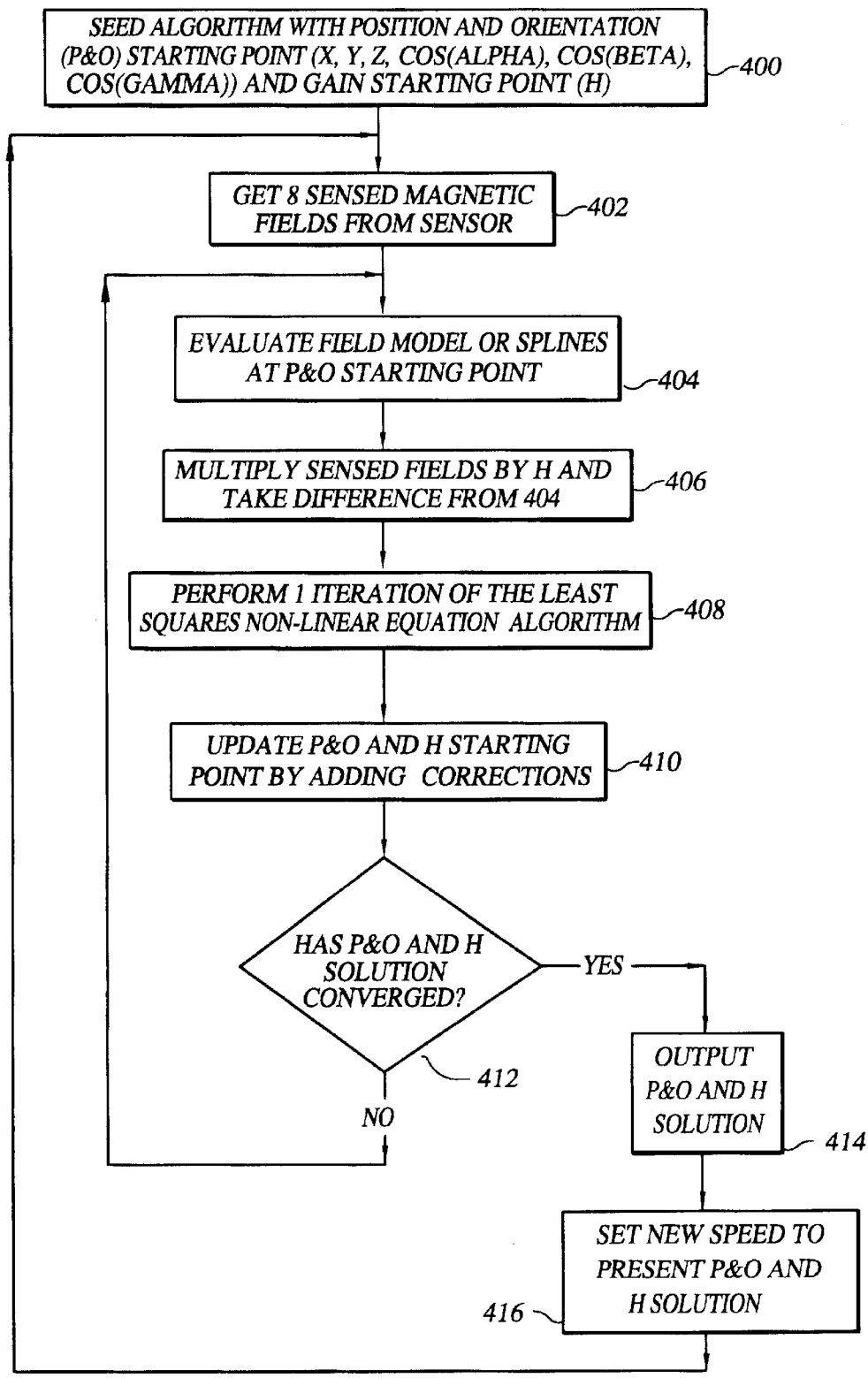
FIG. 12 a simplified flowchart of an automatic calibration technique to adjust for sensor gain and related factors.

FIG. 12 flowcharts the mechanism for using automatic calibration within a magnetic tracking system. In block 400 an initial starting point for the position and orientation algorithm is chosen consisting of position and orientation and a gain ratio (H). H represents the ratio of the assumed sensor gain to the true sensor gain and is typically unity. Methods to determine an initial starting point for position and orientation are disclosed by Mark R. Schneider in U.S. Pat. No. 6,073,043, entitled MEASURING POSITION AND ORIENTATION USING MAGNETIC FIELDS or any other applicable methods. Block 402 obtains the sensed magnetic fields from the sensor due to the 8 field generators. This signal conditioning process is detailed in the aforementioned patent. Blocks 404–412 form the basis of the non-linear equation solver based on the method of least squares. In block 404 the magnetic field models or splines are evaluated at the position and orientation starting point. This yields a predicted set of magnetic field readings. Block 406 multiplies the sensed fields by H and subtracts them from the results of block 404. In block 408 the differences from block 406 drives the least squares algorithm to make a correction to the starting point. This is indicated by block 410. The correction is in a direction intended to reduce the square root of the sum of the squares of the differences between the sensed magnetic fields multiplied by H and the predicted values. Block 412 decides whether the corrected position and orientation and gain satisfies certain convergence criteria, indicating the solution has been reached. If the solution has not been reached then the corrected starting point becomes the new starting point and the process repeats through blocks 404–412 until convergence is achieved.

When convergence occurs the value of the position, orientation and gain solution that caused convergence is output. This output then becomes the new seed position, orientation and gain in block 416 and the entire process starts over at block 402.

It has been observed that when tracking in a highly distorted environment the automatic calibration changes drastically. This can be used as an indicator of a distorted environment.

Increasing Update Rate with Time Multiplexed Excitations

Figure 13:
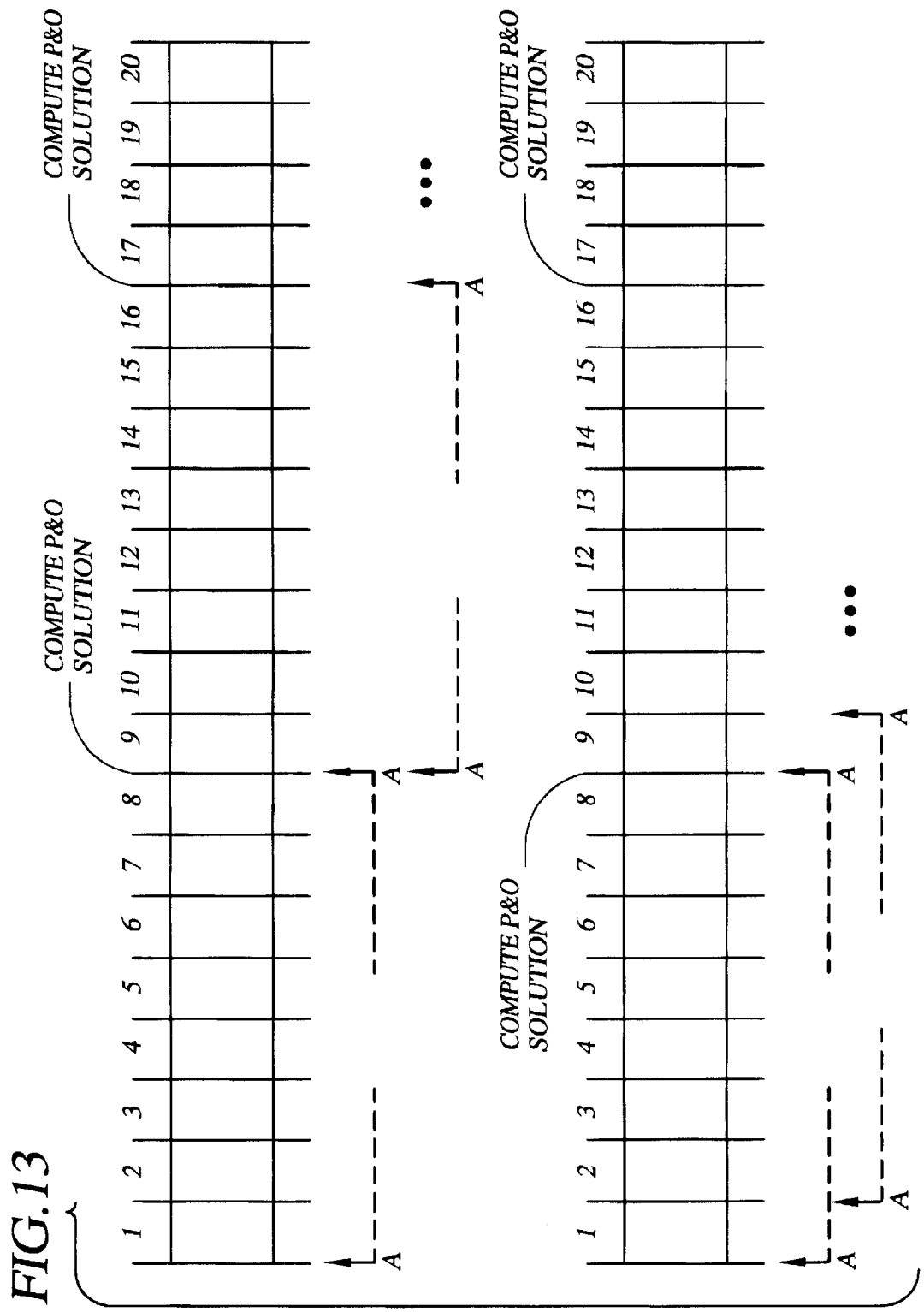
FIG. 13 illustrates a multiplex technique that can be used with the invention.

The basic operation of all magnetic tracking systems is 1) generate a plurality of separable magnetic fields; 2) sense the induced voltages at the sensing transducers or antennas; and 3) calculate position and orientation (P&O) from this data. In systems with time multiplexed field generation the entire sequence of all the induced sensor voltages must be captured before a P&O solution is generated. Therefore the update rate of the P&O solution is based on the time it takes to measure all the induced voltages. A method for increasing the update rate is to always use a sliding set of measurements and feed this into the technique. For example, if 8 time multiplexed excitations take 8 milliseconds each then it takes 64 milliseconds (update rate=1/.064=15.625 Hz) before a solution comprised of the 8 measurements can be calculated. However, if after each excitation the last 8 pieces of data are used in the technique the update time is only 8 milliseconds (125 Hz). This is illustrated in the simplified drawing of FIG. 13.

In the present embodiment, there are 8 excitations of which four excitations are frequency multiplexed and the two sets of four frequency multiplexed excitations are time multiplexed. A solution can be calculated using the latest two sets of frequency multiplexed data. This yields an update rate that is double the original data processing scheme. However, it will be appreciated, by those skilled in the art, that any one of a number of suitable sliding data schemes may be employed.

Coil Error Compensation

Figure 14:
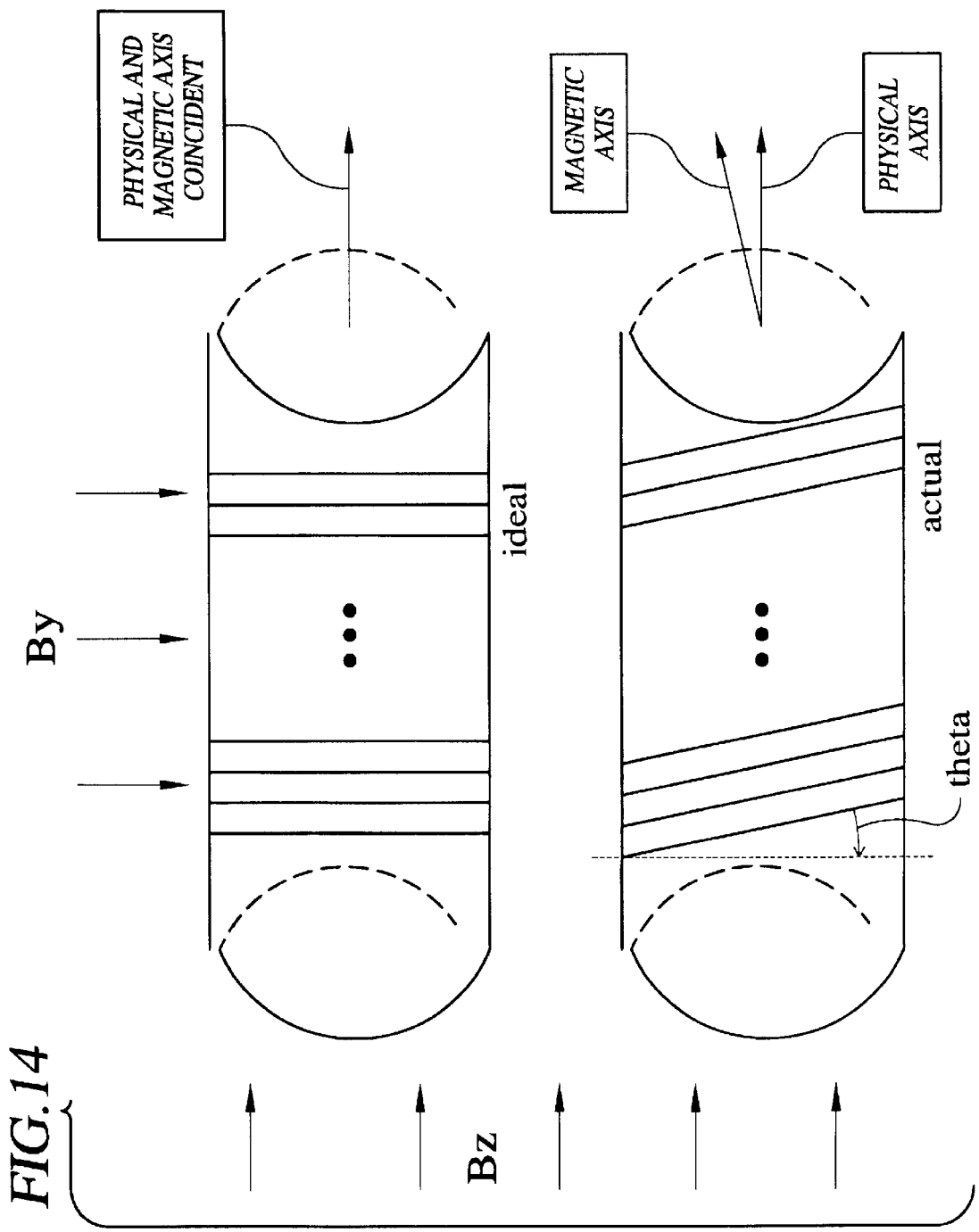
FIG. 14 shows an ideal sensing coil and an actual sensing coil for purposes of comparison.

Due to the nature of 5DOF tracking (the use of a single sensing coil) the sensing coil must be as "perfect" as possible. One of the difficulties in using very small, multi-turn sensing coils is the effect due to winding pitch. Pitch comes about because of the spiral nature of coil winding; it is helical. This is illustrated in FIG. 14.

The winding pitch is dependent on the wire gauge. For example, a loop of diameter 0.063" of 42 gauge wire (wire diameter=0.0025") has a winding pitch of approximately 2.3. If this coil is placed in a field having $B_y$ and $B_z$, components as shown, the induced voltage for the actual coil is approximately proportional to $B_z$ +theta* $B_y$, while for the ideal case the induced voltage for the coil is proportional to $B_z$.

Figure 15:
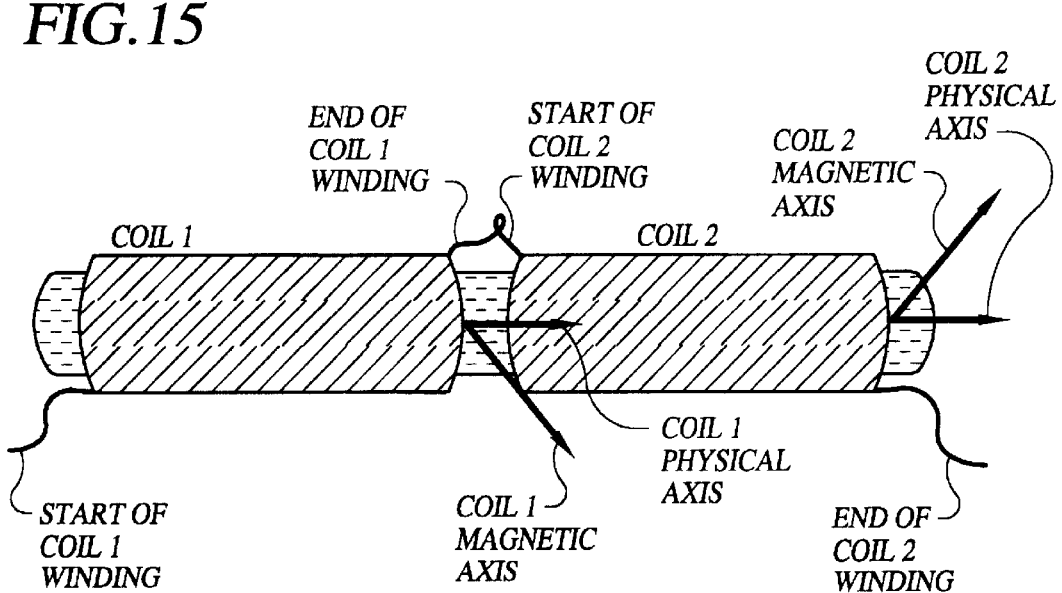
FIG. 15 is a simplified illustration of a sensing coil arrangement that provides improved accuracy.

To fix this problem one can take two separate half length coils, wire them in series but align them such that the magnetic axis of one plus the magnetic axis of the other average out to being coincident with their physical axes. This is shown in FIG. 15. Such an alignment can be performed within a helmholtz apparatus.

Figure 16:
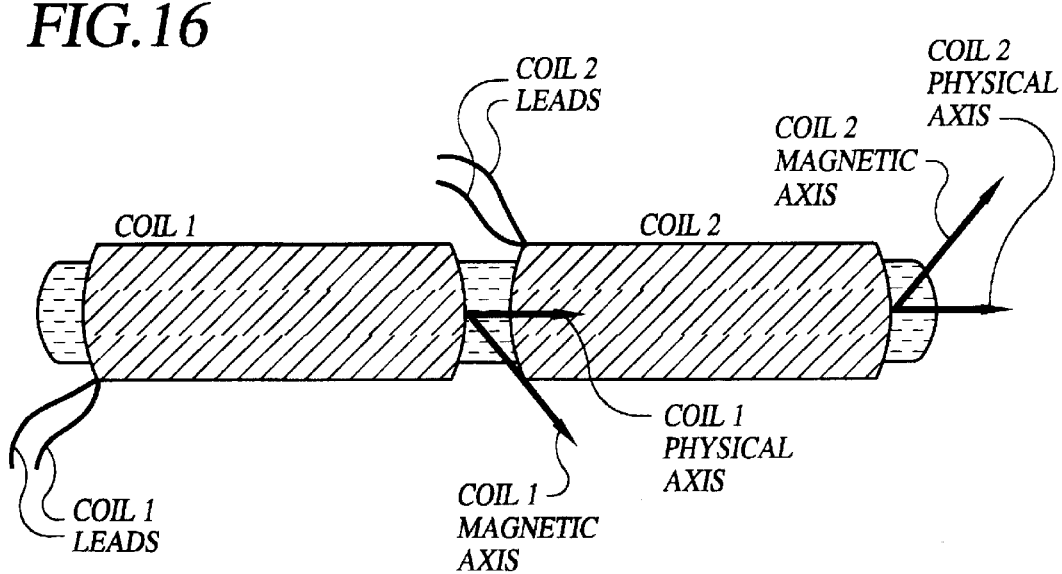
FIG. 16 is a simplified illustration of an alternate sensing coil arrangement that provides improved accuracy.

An interesting twist to the concept shown in FIG. 15 is illustrated in FIG. 16. Instead of wiring the coils in series, effectively summing their outputs, one can bring both sets of sensed signals back separately and process them in a 6DOF tracking algorithm, as disclosed by Mark R. Schneider in U.S. Pat. No. 6,073,043, entitled MEASURING POSITION AND ORIENTATION USING MAGNETIC FIELDS. In this usage it is advantageous to maximize the winding pitch.

The advantage to this method is that the sensing coils are physically colinear. All other 6DOF magnetic tracking systems that use coils of wire as sensing devices use orthogonal coils. Orthogonal coils take up more space and are not as desirable in catheter applications. Another benefit with the colinear design is that instrumentation can go through the center of the coils, unlike orthogonal coils.

It will be appreciated, by those skilled in the art, that any one of a number of suitable coil winding techniques can be employed to improve tracking accuracy and/or functionality, including changing the winding pitch on alternate layers of the coil. It should also be obvious that these techniques can be applied to field generating coils to more effectively align their magnetic axes to their physical axes.

Although specific constructions have been presented herein, it is to be understood that these are for illustrative purposes only. Various modifications and adaptations will be apparent to those of skill in the art. In view of possible modifications, it will be appreciated that the scope of the present invention should be determined by reference to the claims appended hereto.

What is claimed is:

1. A remote object location determining system comprising:
    a generation subsystem having at least one transducer operable to produce an electromagnetic field;
    a sensing subsystem having at least one transducer operable to measure an electromagnetic field produced by the generation subsystem;
    a driver operable to apply excitation waveforms to the generation subsystem; and
    a processor operably connected to receive sensor signals from the sensing subsystem, and to determine at least two location parameters by comparing measured magnetic field values to a function of splines corresponding to magnetic field values; and
wherein at least one of the generation subsystem and the sensing subsystem has a plurality of transducers.

2. The remote object location determining system of claim 1 wherein the processor has stored splines from measurements taken using known locations prior to using the system for determining unknown location parameters.

3. The remote object location determining system of claim 2 wherein the processor uses an iteration technique to determine the at least two location parameters.

4. The remote object location determining system of claim 1 wherein the generation subsystem includes a plurality of transducers operable to produce electromagnetic fields and wherein the driver sequentially drives different transducers of the generation subsystem in a multiplexing operation.

5. The remote object location determining system of claim 1 wherein the system is a medical system for use on a patient with one of the generating subsystem and sensing subsystem inside the patient and the other of the generating subsystem and sensing subsystem outside the patient.

6. The remote object location determining system of claim 1 further comprising a catheter operable for endomyocardial revascularization and wherein one of the generation subsystem and sensing subsystem is on or in the catheter.

7. The remote object location determining system of claim 6 wherein the processor has a plurality of magnetic field values stored from initial measurements and determines location parameters by comparing measured magnetic field values to a function of stored splines.

8. The remote object location determining system of claim 7 wherein the processor determines gain in the sensing subsystem automatically and determines location parameters independent from any variations in the gain of the sensing subsystem.

9. The remote object location determining system of claim 1 wherein the processor minimizes inaccuracies in the location parameters by performing eddy current compensation, thus reducing or eliminating inaccuracies that would otherwise be introduced by eddy currents in the vicinity of the sensing subsystem and the generation subsystem.

10. The remote object location determining system of claim 1 wherein the processor determines gain in the sensing subsystem automatically and determines location parameters independent from any variations in the gain of the sensing subsystem.

11. The remote object location determining system of claim 10 wherein the system is a medical system for use on a patient, the location parameters providing information used in a process of treating or diagnosing a patient.

12. The remote object location determining system of claim 11 wherein the medical system is operable for use on a patient with one of the generating subsystem and sensing subsystem inside the patient and the other of the generating subsystem and sensing subsystem outside the patient.

13. The remote object location determining system of claim 12 further comprising a catheter and wherein one of the generation subsystem and sensing subsystem is on or in the catheter.

14. The remote object location determining system of claim 13 wherein the catheter is operable for endomyocardial revascularization.

15. The remote object location determining system of claim 14 wherein the catheter is a laser catheter operable for endomyocardial revascularization.

16. A remote object location determining system comprising:
    a generation subsystem having at least one transducer operable to produce an electromagnetic field;
    a sensing subsystem having at least one transducer operable to sense an electromagnetic field produced by the generation subsystem;
    a driver operable to apply excitation waveforms to the generation subsystem; and
    a processor operably connected to receive sensor signals from the sensing subsystem, the processor operable to determine at least two location parameters of a relationship between the generation subsystem and the sensing subsystem, and wherein the processor determines gain in the sensing subsystem automatically and determines location parameters independent from any variations in the gain of the sensing subsystem; and
wherein at least one of the generation subsystem and the sensing subsystem has a plurality of transducers.

17. The remote object location determining system of claim 16 wherein the system is a medical system for use on a patient, the location parameters providing information used in a process of treating or diagnosing a patient.

18. The remote object location determining system of claim 17 wherein the medical system is operable for use on a patient with one of the generating subsystem and sensing subsystem inside the patient and the other of the generating subsystem and sensing subsystem outside the patient.

19. The remote object location determining system of claim 18 further comprising a catheter and wherein one of the generation subsystem and sensing subsystem is on or in the catheter.

20. The remote object location determining system of claim 19 wherein the catheter is operable for endomyocardial revascularization.

21. The remote object location determining system of claim 20 wherein the catheter is a laser catheter operable for endomyocardial revascularization.

22. The remote object location determining system of claim 17 wherein the excitation waveforms are selected from the group consisting of a ramp waveform and a triangular waveform, and wherein at least one of the generation subsystem and the sensing subsystem has a plurality of transducers and wherein the processor minimizes inaccuracies in the location parameters by performing eddy current compensation, thus reducing or eliminating inaccuracies that would otherwise be introduced by eddy currents in the vicinity of the sensing subsystem and the generation subsystem.

23. The remote object location determining system of claim 17 processor operably connected to receive sensor signals from the sensing subsystem, and to determine at least two location parameters by comparing measured magnetic field values to a function of splines corresponding to magnetic field values.

24. A remote object location determining system comprising:

a generation subsystem having at least one transducer operable to produce an electromagnetic field;

a sensing subsystem having at least one transducer operable to sense an electromagnetic field produced by the generation subsystem;

a driver operable to apply excitation waveforms to the generation subsystem, the excitation waveforms being selected from the group consisting of a ramp waveform and a triangular waveform; and a processor operably connected to receive sensor signals from the sensing subsystem, the processor operable to determine at least two location parameters of a relationship between the generation subsystem and the sensing subsystem; and wherein at least one of the generation subsystem and the sensing subsystem has a plurality of transducers and wherein the processor minimizes inaccuracies in the location parameters by performing eddy current compensation, thus reducing or eliminating inaccuracies that would otherwise be introduced by eddy currents in the vicinity of the sensing subsystem and the generation subsystem.

25. The remote object location determining system of claim 24 wherein the generation subsystem includes a plurality of transducers operable to produce electromagnetic fields and wherein the driver sequentially drives different transducers of the generation subsystem in a multiplexing operation.

26. The remote object location determining system of claim 25 wherein the processor performs eddy current compensation by a non-extrapolated calculating of a response at infinite time of the sensor signals.

27. The remote object location determining system of claim 24 wherein the system is a medical system for use on a patient with one of the generating subsystem and sensing subsystem inside the patient and the other of the generating subsystem and sensing subsystem outside the patient.

28. The remote object location determining system of claim 27 further comprising a catheter operable for endomyocardial revascularization and wherein one of the generation subsystem and sensing subsystem is on or in the catheter.

29. The remote object location determining system of claim 27 processor operably connected to receive sensor signals from the sensing subsystem, and to determine at least two location parameters by comparing measured magnetic field values to a function of splines corresponding to magnetic field values.

30. The remote object location determining system of claim 27 wherein the processor determines gain in the sensing subsystem automatically and determines location parameters independent from any variations in the gain of the sensing subsystem.

31. A method of determining the position and orientation of a remote object, comprising the steps of:

measuring a magnetic field so as to generate first measurement values;

characterizing said magnetic field with splines using said first measurement values;

measuring said magnetic field at a selected location so as to generate second measurement values; and determining at least two location parameters relative to said selected location by comparing said second measurement values with said splines.

32. A method according to claim 31, wherein second location is inside a mammalian body.

33. A method according to claim 31, wherein said at least two location parameters include position and orientation information.

34. A system for determining the location of a remote object, comprising:

a generation subsystem having at least one transducer operable to produce a magnetic field;

a sensing subsystem having at least one transducer operable to measure a magnetic field produced by the generation subsystem;

a driver operable to apply excitation waveforms to the generation subsystem;

a processor operably connected to receive sensor signals from the sensing subsystem, and to determine at least two location parameters by comparing measured magnetic field values to a plurality of polynomials fit together to characterize said electromagnetic field; and wherein at least one of the generation subsystem and the sensing subsystem has a plurality of transducers.

35. A remote object location determining system, comprising:

first means for producing a magnetic field;

second means for measuring a magnetic field produced by said first means and providing an output signal containing magnetic field values obtained from measurement of said magnetic field;

third means for applying excitation waveforms to said first means; and fourth means, operably connected to said second means, for receiving said output signal and for determining at least two location parameters by comparing said magnetic field values in said output signal to a function of splines characterizing said magnetic field produced by said first means.

* * * * *